(12) United States Patent
Handelsman et al.

(10) Patent No.: US 8,063,108 B2
(45) Date of Patent: Nov. 22, 2011

(54) METHOD FOR MODULATING MICROBIAL QUORUM SENSING

(75) Inventors: Jo E. Handelsman, Madison, WI (US); Bradley R. Borlee, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 12/712,948

(22) Filed: Feb. 25, 2010

(65) Prior Publication Data

US 2010/0216835 A1 Aug. 26, 2010

Related U.S. Application Data

(63) Continuation of application No. 10/907,166, filed on Mar. 23, 2005, now abandoned.

(60) Provisional application No. 60/555,307, filed on Mar. 23, 2004.

(51) Int. Cl.
*A01N 35/00* (2006.01)
*A01N 33/18* (2006.01)
*A01N 33/24* (2006.01)
*A61K 31/12* (2006.01)
*A61K 31/04* (2006.01)

(52) U.S. Cl. ........................................ 514/688; 514/741

(58) Field of Classification Search .................. 514/688, 514/741
See application file for complete search history.

(56) References Cited

U.S. PATENT DOCUMENTS 2,518,154 A    8/1950  Lewenstein

OTHER PUBLICATIONS

The American Heritage Dictionary of the English Language, 2007, Houghlin Mifflin Company.*
Miller MB and Bassler BL. Quorum sensing in bacteria. Annual Reviews in Microbiology. 2001; 55:165-99.*
Andersen et al., Appl. Environ. Microbio. 67:575-85 (2001).
Bassler et al., Mol. Microbiol. 9:773-786 (1993).
Bassler et al., Mol. Microbiol. 13:273-286 (1994).
Bassler et al., Microbiol. 431-435 (1995).
Beck Von Bodma, 1998 Proc. Natl. Acad. Sci. USA 95:7687-7692.
Costerton et al., Ann. Rev. Microbiol. 49:711-745 (1995).
Davies et al., Science 280:295-298 (1998).
De Kievit et al., Infect. Immun. 68:4839-4849 (2000).
Eberl, Syst. Appl. Microbiol. 22:493-506 (1999).
Fray et al., Nat. Biotechnol. 171:1017-1020 (1999).
Fuqua et al., Ann. Rev. Microbiol. 50:727-751 (1996).
Fuqua et al., Curr. Opion Microbiol. 1:183-189 (1998).
Govan et al., Microbiol. Rev. 60:539-574 (1996).
Hentzer et al., J. Clin. Invest. 112:1300-7 (2003).
Huber et al., Microbiol. 147:2517:2528 (2001).
Lewis, Antimicrob. Agents Chemother. 45:999-1007 (2001).
Mae et al., Mol. Plant Microbe Interact. 14:1035-1042 (2001).
McClean et al., Microbiology 143(Part 12):3703-3711 (1997).
Pearson et al., J. Bacteriol. 179:5756-67 (1997).
Rand et al., Methods Cell Bioi 48:187-204 (1995).
Rasmussen et al., J. Bacteriol. 187: 1799-814 (2005).
Steidle et al., Appl. Environ. Microbiol. 67:5761-70 (2001).
Stickler et al., Appl. Environ. Microbiol. 64:3486-3490 (1998).
Teplitski et al. Mol. Plant Microbe Interact. 13:637-648 (2000).
Van Delden et al., Emerg. Infect. Dis. 4: 551-60 (1998).
Whitehead et al., Microbiol. Rev. 25:365-404 (2001).
Zhu et al. 2003 Applied and Environmental Microbiology, vol. 69, No. 11, p. 6949-6953.
Pisetsky and St Clair, "Progress in the treatment of rheumatoid arthritis" 2001 Journal of the American Medical Association, 286(22), 2787-2790.

* cited by examiner

*Primary Examiner* — San-Ming Hui
*Assistant Examiner* — Paul Zarek
(74) *Attorney, Agent, or Firm* — Quarles & Brady LLP

(57) ABSTRACT

The present invention provides compositions and methods for modulating bacterial quorum sensing using antagonist or agonist compounds. Further, the present invention provides methods of treating or preventing microbial damages and diseases, in particular for diseases where there is an advantage in inhibiting quorum sensing regulated phenotypes of pathogens.

22 Claims, 21 Drawing Sheets

A  Acyl-Homoserine Lactone Autoinducers (AHLs)
*V. fischeri*/LuxI
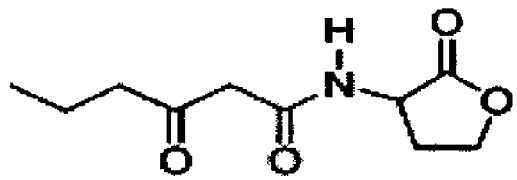
*P. aeruginosa*/LasI
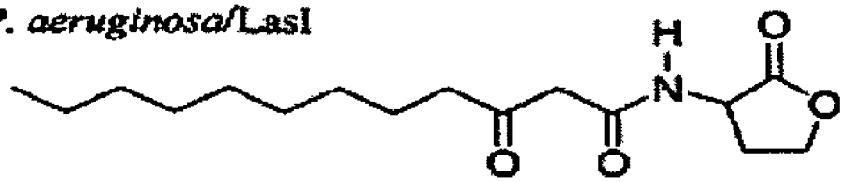
*P. aeruginosa*/RhlI
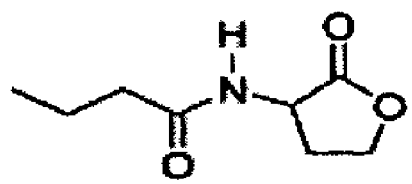
*P. stewartii*/EsaI
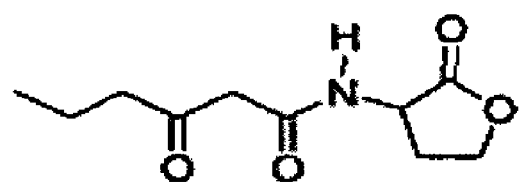
*V. harveyi*/LuxLM
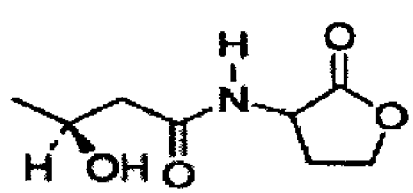
FIGURE 1A

B  Oligopeptide Autoinducers
*B. subtilis*/ComX                 ADPITRQ*WGD
*B. subtilis*/CSF                   ERGMT
*S. aureus*/subgroup 1          YSTCDFIM (thiolactone cyclized M to C)
*S. aureus*/subgroup 2          GVNACSSLF (thiolactone cyclized F to C)
*S. aureus*/subgroup 3          YINCDFLL (thiolactone cyclized L to C)
*S. aureus*/subgroup 4          YSTCYFIM (thiolactone cyclized M to C)
C  AI-2
*V. harveyi*/LuxS
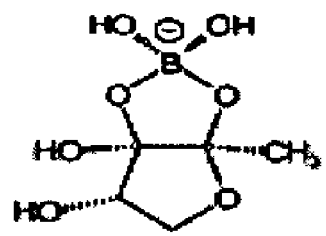
FIGURE 1 B and 1C

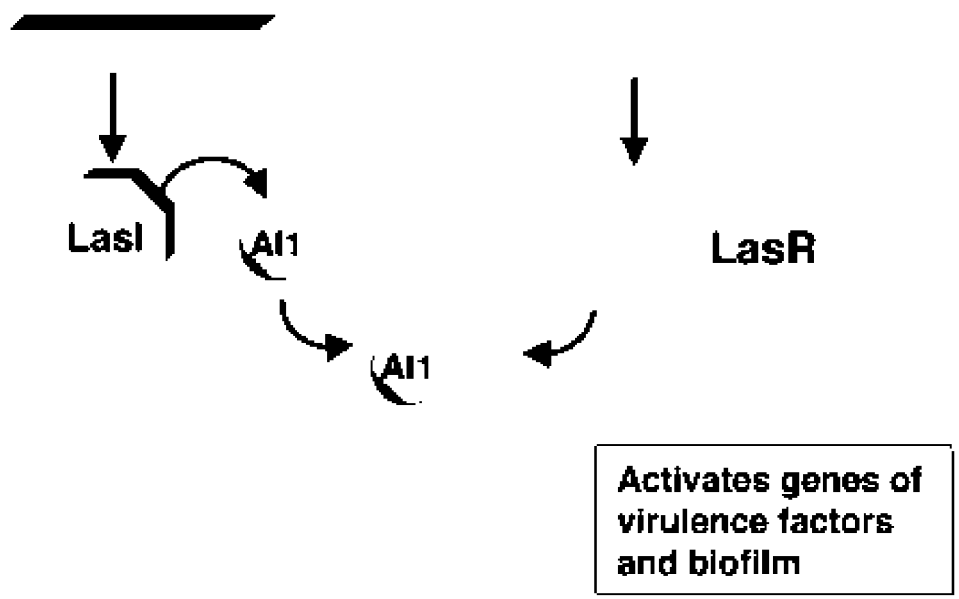
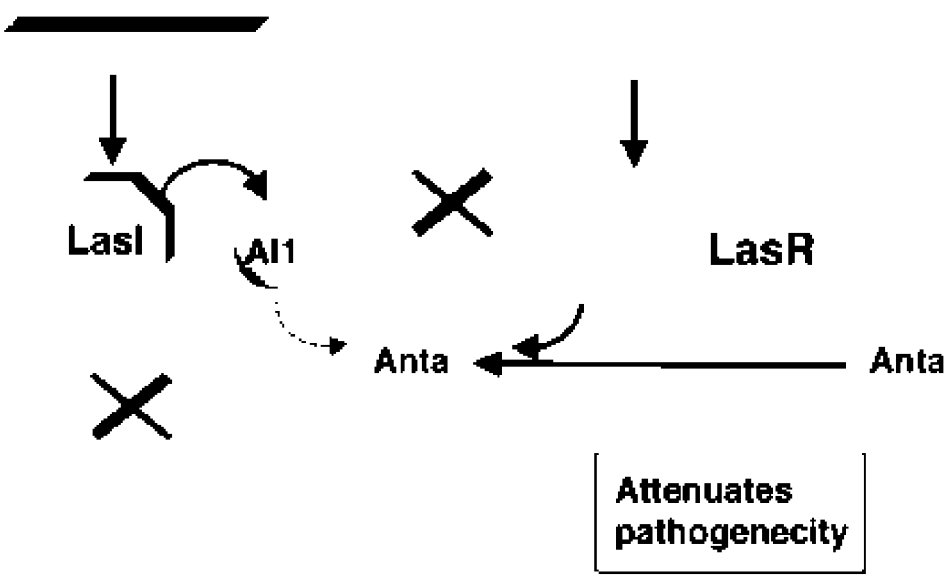
Fig. 3

Antagonists
5947920
5174514
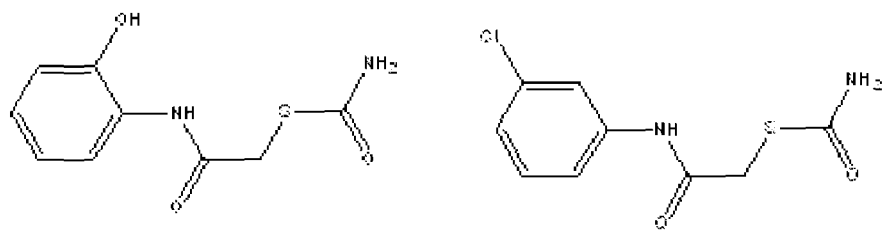
5133201
6240194
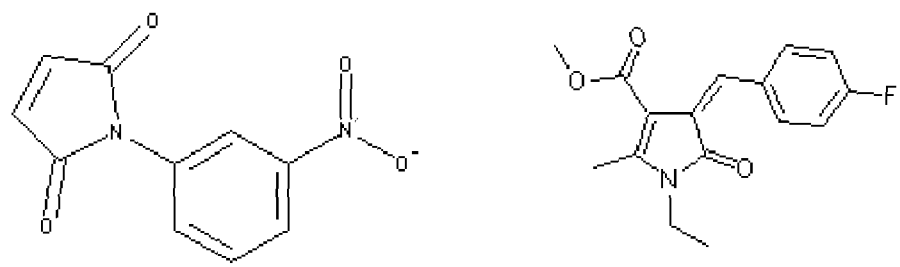
5854800
5214835
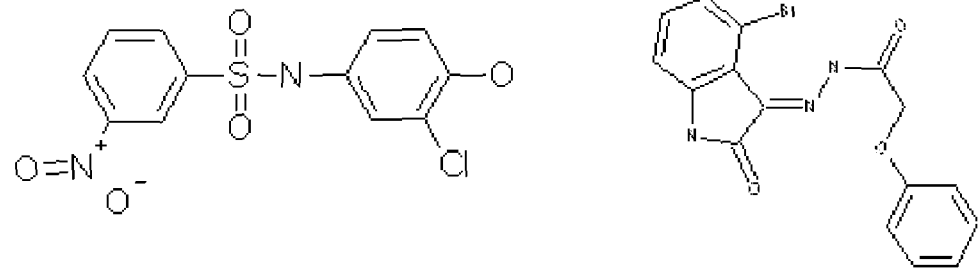
FIGURE 5A

5952120
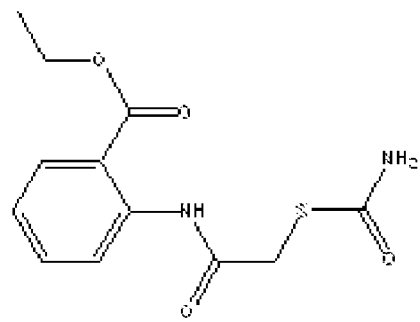
5953997
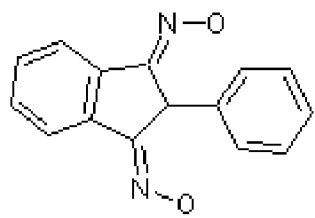
5117815
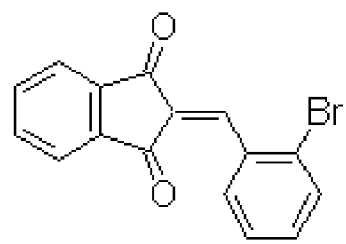
FIGURE 5B

Agonists

Fig. 14 Antagonists vs. increasing concentrations of 3oxoC12HSL

Fig. 15 10 μM Antagonists vs. 3oxoC12HSL

Thiocarbamate substructure
Activity similar to compound# 5947920
| | |
|---|---|
| Chemical Name: | Carbamothioic acid, S-[2-oxo-2-(phenylamino)ethyl] ester |
| Registry Number: | 5428-95-5 |
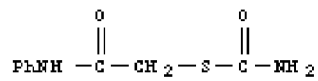
| | |
|---|---|
| Pricing: | Quantity : N/A, Price: contact supplier |
| Company Info: | TimTec, Inc.<br>100 Interchange Blvd.<br>Newark, DE, 19711<br>USA<br>Phone: (302) 292-8500<br>Fax: (302) 292-8520<br>Email: info@timtec.net |
| Web: | http://www.timtec.net |
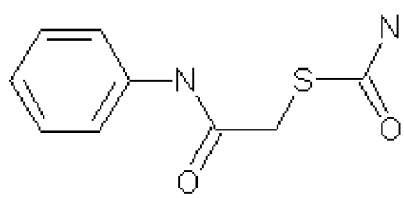
Fig. 16

| | |
|---|---|
| 5117815 | 2-(2-bromobenzylidene)-1H-indene-1,3(2H)-dione |
| 5133201 | 1-(3-nitrophenyl)-1H-pyrrole-2,5-dione |
| 5174514 | 2-phenyl-1H-indene-1,3(2H)-dione dioxime |
| 5214835 | N'-(4-bromo-5-methyl-2-oxo-1,2-dihydro-3H-indol-3-ylidene)-2-phenoxyacetohydrazide |
| 5854800 | N-(3-chloro-4-hydroxyphenyl)-3-nitrobenzenesulfonamide |
| 5952120 | ethyl 2-({[(aminocarbonyl)thio]acetyl}amino)benzoate |
| 5953997 | S-{2-[(3-chlorophenyl)amino]-2-oxoethyl} thiocarbamate |
| 5947920 | S-{2-[(2-hydroxyphenyl)amino]-2-oxoethyl} thiocarbamate |
| 6240194 | methyl 1-ethyl-4-(4-fluorobenzylidene)-2-methyl-5-oxo-4,5-dihydro-1H-pyrrole-3-carboxylate |
| | |
| 5180207 | N,N'-diphenylisophthalamide |
| 5724068 | N-[5-(anilinocarbonyl)-2-methoxyphenyl]-3,4-dichlorobenzamide |
| 5802569 | N-(2-methoxydibenzo[b,d]furan-3-yl)-2-nitrobenzamide |
| 5836366 | N-[2-(2-methylphenyl)-1,3-benzoxazol-5-yl]-2-nitrobenzamide |
| 5847828 | 5-(4-bromophenyl)-N-[3-(1H-imidazol-1-yl)propyl]-7-(trifluoromethyl)pyrazolo[1,5-a]pyrimidine-3-carboxamide |
| 5866902 | 2-cyano-N-(4-methoxyphenyl)-3-[5-(2-methyl-5-nitrophenyl)-2-furyl]acrylamide |
| 5878890 | 3-[5-(4-chlorophenyl)-2-furyl]-2-cyano-N-(4-methoxyphenyl)acrylamide |
| 5881861 | 2-cyano-3-[4-(diethylamino)-2-methoxyphenyl]-N-phenylacrylamide |
| 5883374 | methyl 5-{5-[2-(1H-benzimidazol-2-yl)-2-cyanovinyl]-2-furyl}-2-chlorobenzoate |
| 5884492 | methyl 5-[5-(3-anilino-2-cyano-3-oxo-1-propen-1-yl)-2-furyl]-2-chlorobenzoate |
| 6024883 | N-(4-acetylphenyl)-5-(4-bromophenyl)-2-furamide |
| 6030543 | N-[4-chloro-3-(6-methyl-1,3-benzoxazol-2-yl)phenyl]-2-thiophenecarboxamide |
| 6074181 | N-(4-acetylphenyl)-5-(4-ethoxyphenyl)-7-methylpyrazolo[1,5-a]pyrimidine-2-carboxamide |
| 6239730 | N-(2-[5-(2,5-dichlorophenyl)-2-furyl]-1-{[(3-pyridinylmethyl)amino]carbonyl}vinyl)-4-methylbenzamide |

Fig. 17

METHOD FOR MODULATING MICROBIAL QUORUM SENSING

CROSS REFERENCE TO RELATED APPLICATIONS

This application is a continuation of U.S. application Ser. No. 10/907,166, filed on Mar. 23, 2005, now abandoned which claims the benefit of U.S. Application No. 60/555,307, filed on Mar. 23, 2004, both of which are incorporated by reference herein in their entirety.

STATEMENT REGARDING FEDERALLY SPONSORED RESEARCH OR DEVELOPMENT

This invention was made with United States government support awarded by the following agencies: National Institutes of Health/CREES—Grant No. 02-CHRF-0-6055. The United States government has certain rights in this invention.

BACKGROUND OF THE INVENTION

The present invention generally relates to quorum sensing and specifically relates to methods for modulating bacterial quorum sensing using antagonist or agonist compounds, and to methods of treating or preventing microbial damages and diseases, in particular for diseases where there is an advantage in inhibiting quorum sensing regulated phenotypes of pathogens.

Many microbial pathogens cause tremendous damages worldwide, in humans as well as in animals and crop plants. The continuing emergence of multiple-drug-resistant pathogen strains has necessitated finding new compounds that can be used in antimicrobial treatment. In general, two strategies exist for controlling the pathogens: either to kill the pathogen or to attenuate its virulence such that it does not cause damages to the host.

The latter approach has the advantage of not creating selective pressure in favor of drug resistant strains. Antimicrobial compounds having virulence—attenuating but not cell-killing effects are expected to remain effective for longer period of time than conventional antibiotics because of the lack of development of drug resistance. This approach has, however, suffered from a lack of specific targets for rational drug design.

The bacterial quorum-sensing regulatory system offers such a novel target. The control of gene expression in response to cell density, or quorum sensing, was first described in the marine luminous bacteria *Vibrio fischeri* and *Vibrio harveyi*. This phenomenon has recently become recognized as a general mechanism for gene regulation in many Gram negative bacteria. Quorum sensing bacteria synthesize, release, and respond to specific acyl-homoserine lactone ("AHL" or "HSL") signaling molecules called autoinducers ("AI") to control gene expression as a function of cell density.

Except that of *V. harveyi*, all acyl-homoserine lactone quorum sensing systems described to date utilize an autoinducer synthase encoded by a gene homologous to luxI of *V. fischeri*, and response to the autoinducer is mediated by a transcriptional activator protein encoded by a gene homologous to luxR of *V. fischeri* (Bassler and Silverman, in Two component Signal Transduction, Hoch et al., eds, Am. SOC. Microbiol. Washington D.C., pp 431-435, 1995).

*V. harveyi* has two independent density sensing systems (Signaling Systems 1 and 2), and each is composed of a sensor-autoinducer pair. Signaling System 1 is composed of Sensor 1 and autoinducer 1 (AI-1), which is N(3-hydroxybutanoyl)-L-homoserine lactone (see Bassler et al., Mol. Microbiol. 9: 773-786, 1993). Signaling System 2 is composed of Sensor 2 and autoinducer 2 (AI-2) (Bassler et al., Mol. Microbiol. 13: 273-286, 1994). Signaling System 1 is a highly specific system proposed to be used for intra-species communication and Signaling System 2 appears to be less species selective, and is hypothesized to be for inter-species communication (Bassler et al., J. Bacteriol. 179: 4043-4045, 1997).

In recent years it has become apparent that many Gram negative bacteria employ one or more quorum sensing systems comprising HSL derivatives with different acyl side chains to regulate in a cell-density dependent manner a wide variety of physiological processes such as swarming motility, biofilm formation, pathogenicity, conjugation, bioluminescence or production of pigments and antibiotics (for reviews and references see, e.g.: Fuqua et al., 1996, Ann. Rev. Microbiol. 50:727-51; Fuqua et al., 1998, Curr. Opinion Microbiol. 1:183-89, 1998; Eberl, 1999, Syst. Appl. Microbiol. 22:493-506; and De Kievit et al., 2000, Infect. Immun. 68:4839-49).

The quorum sensing system is an attractive antibacterial target because it is not found in humans and is critical for high level bacterial virulence. Targeting quorum sensing could have far reaching implications for treatment of many human pathogens that use quorum sensing virulence regulation, such as species of *Bordetella, Enterobacter, Pseudomonas aeruginosa, Serratia*, and *Yersinia*.

Recent studies in vivo have shown that the virulence of *Pseudomonas aeruginosa* lacking one or more genes responsible for quorum sensing is attenuated in its ability to colonize and spread within the host. Similarly, elimination of the AHL synthase in several plant pathogenic bacteria has lead to complete loss of infectivity (Beck von Bodman, 1998, Proc. Natl. Acad. Sci. USA 95:7687-7692; Whitehead et al., 2001, Microbiol. Rev. 25:365-404). Moreover, ectopic expression of AHL synthases in transgenic plant systems has demonstrated that when invading bacteria encounter inducing levels of AHLs, their behaviors are sufficiently modulated to shift the delicate balance of host-microbe interactions in favor of disease resistance (Fray et al., 1999, Nat. Biotechnol. 171: 1017-1020; Mae et al., 2001, Mol. Plant Microbe Interact. 14:1035-1042). A number of plants, including common crop plants, produce endogenous AHL-mimic compounds, and it is thought that these AHLs are the basis of varying degrees of disease resistance and susceptibility (Teplitski et al., 2000, Mol. Plant Microbe Interact. 13:637-648). In addition, the halogenated furanones produced by some marine algae are known to have a pronounced effect on suppressing marine biofouling.

Nevertheless, currently there are no antibacterial compounds that target bacterial quorum sensing system to reduce bacterial virulence and increase susceptibility to bactericidal antibiotics. Accordingly, it is an objective of the present invention to provide newly identified novel compounds that are antagonists or agonists of bacterial quorum sensing. The present invention further provides methods of modulating bacterial quorum sensing, and methods of treating or preventing bacterial infection using the novel antagonists and agonists of the present invention.

SUMMARY OF THE INVENTION

The present invention generally provides methods and compositions for modulating quorum sensing in a microbe. Specifically, the present invention provides compounds selectively modulating bacterial quorum sensing. Through inhibition of the quorum sensing system the expression of many virulence genes and other phenotypes like swarming motility and biofilm formation are significantly reduced or completely abolished rendering a bacterial population more susceptible to the host immune response or to treatment with traditional antibacterial agents.

In a preferred embodiment, the present invention provides a method for modulating quorum sensing of a bacterium. The method comprises contacting said bacterium with at least one quorum sensing compound selected from the group consisting of:

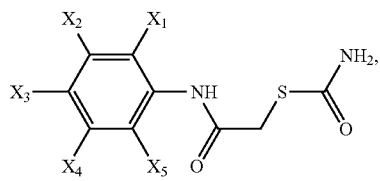

wherein $X_1$, $X_2$, $X_3$, $X_4$, and $X_5$ are independently selected from the group consisting of H, OH, F, Cl, Br, I, $OR_1$, $COOR_1$ and $R_1$, and wherein $R_1$ is $(CH)_nH$ and n is an integer between 0-5;

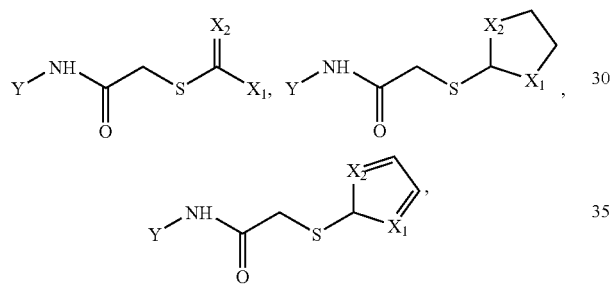

wherein $X_1$ is O, S, or N saturated with hydrogen atoms, $X_2$ is O, Y is selected from a group consisting of a heterocyclic aromatic ring having a nucleophilic group, an aromatic ring having a nucleophilic group, and

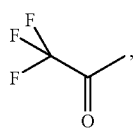

wherein the nucleophilic group is selected from the group consisting of OH, F, Cl, Br, I, OR, $COOR_1$ and $R_1$, wherein $R_1$ is $(CH)_nH$ and n is an integer between 0-5;

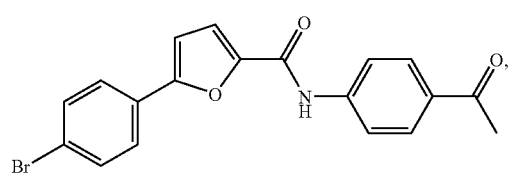

A12

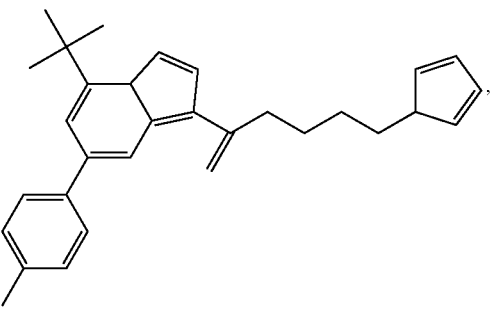

A10

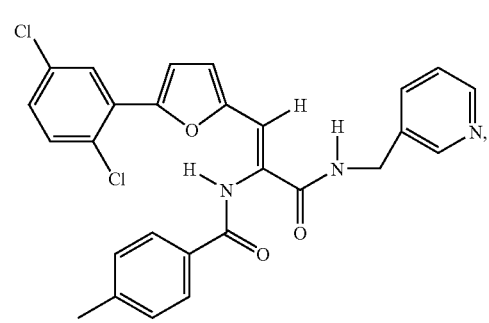

A9

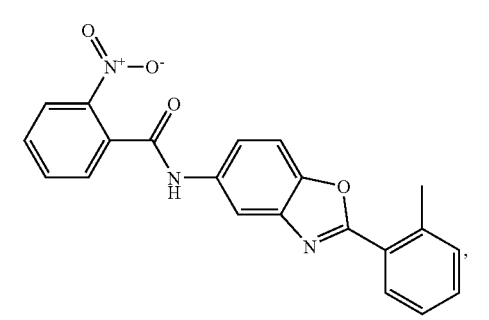

A14

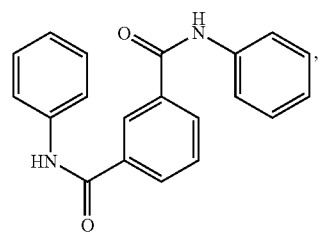

A7

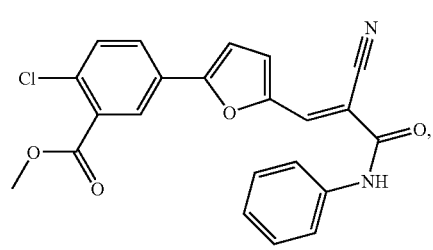

A4

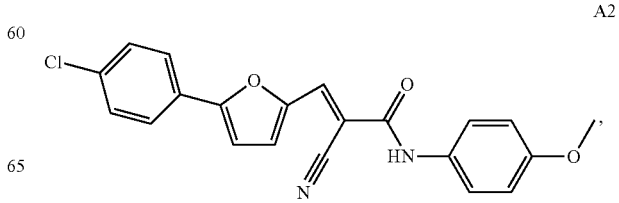

A2

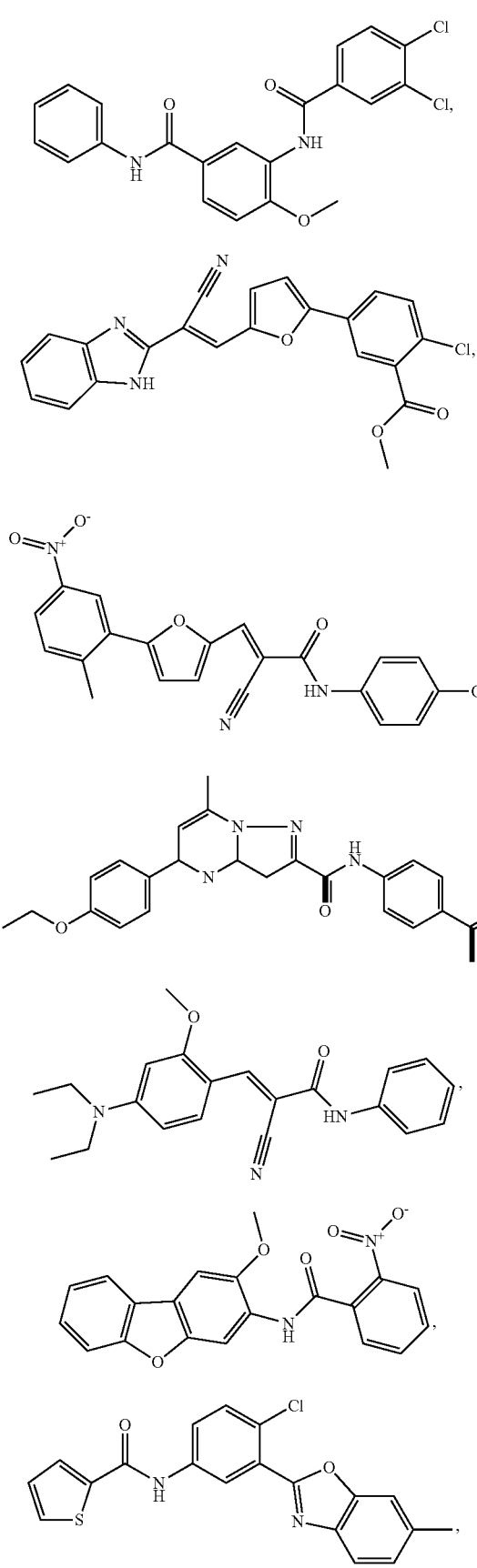
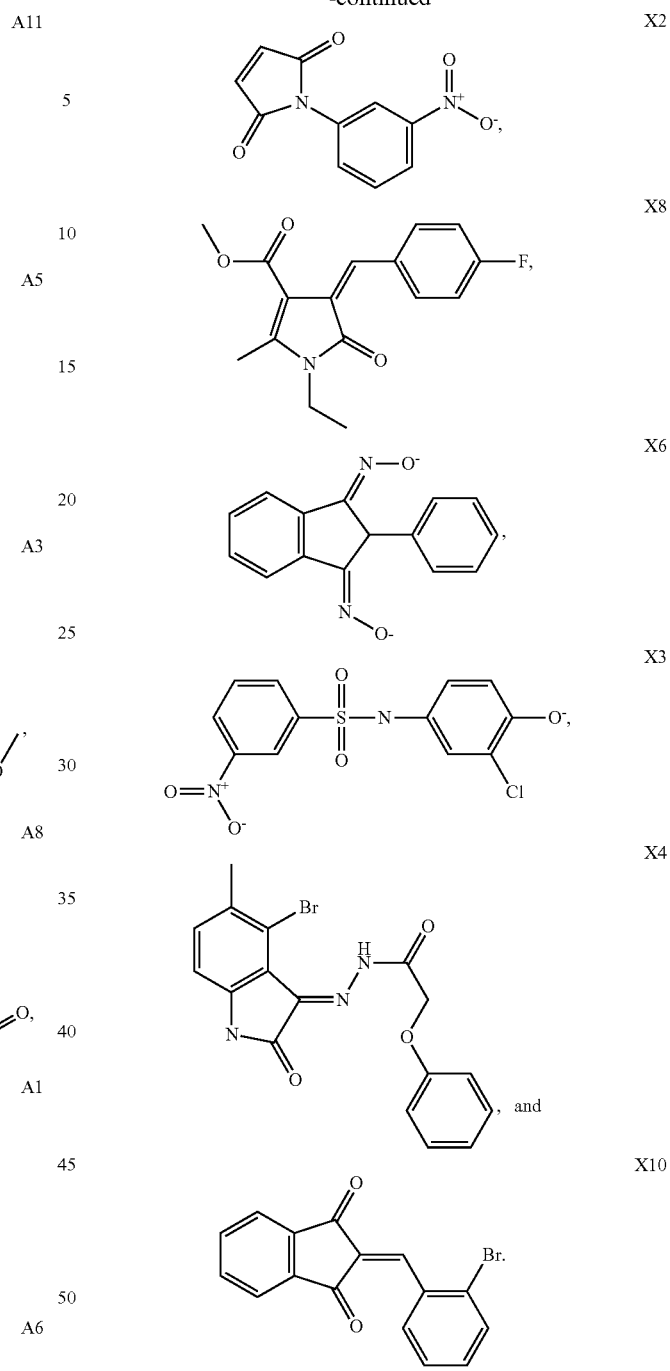

In this method the bacterium is *Pseudomonas aeruginosa*. The method further comprises contacting the bacterium with a suitable antibiotic. The suitable antibiotic may be selected from the group consisting of aminoglycosides, .beta.-lactam antibiotics, and fluoroquinolones.

The present invention further provides a pharmaceutical composition. The pharmaceutical composition includes a pharmaceutically acceptable carrier and a quorum sensing compound or its pharmaceutically acceptable salt as shown above.

In another embodiment, the present invention provides a method for modulating biofilm formation on a surface. This method comprises the step of administering a quorum sensing compound to the surface. In this embodiment, the quorum sensing compounds are as shown above.

Yet another embodiment of the present invention provides a method of regulating microbial disease resistance or susceptibility to a microbial disease in a subject. This method comprises the step of contacting said microbe with a quorum sensing compound, as shown above.

Other objects and advantages of the present invention will be apparent from the detailed description, drawings and claims accompanying the specification.

BRIEF DESCRIPTION OF DRAWINGS

FIG. 1A-C shows the chemical structures of known autoinducers for various bacterial species. FIG. 1A shows the structures of acyl-homoserine lacone autoinducers (AHLs); FIG. 1B shows the structures of oligopeptide autoinducers; FIG. 1C shows the structures of an AI-2 autoinducer.

FIG. 3 is a schematic depiction of signal transduction pathway mediated by autoinducers (top). This pathway is inhibited by antagonists (bottom).

FIGS. 5A and 5B shows a number of quorum sensing antagonists of the present invention.

FIG. 6A shows activity for compounds 592120, 5953997, 5947920; FIG. 6B shows activity for compounds 5174514, 5836366, 6240194, 5133201, 5854800, and 5214835. Although not shown in detail, the antagonists of the present invention are specific to the IasR-P$_{IasI}$-gfp construct, and do not inhibit the GFP expression of the IuxR-P$_{IuxI}$-gfp construct. Furthermore, the antagonists of the present invention are specific to Pseudomonas aeruginosa, as quorum sensing of Chromobacterium violaceum was not affected. Significantly, the antagonists of the present invention only inhibited quorum sensing related gene expression but did not affect bacterial growth as measured by $OD_{600}$.

FIG. 16 provides product data sheet for the Thiocarbamate substructure.

FIG. 17 provides chemical names of selected compounds of the preferred embodiment.

DETAILED DESCRIPTION OF THE INVENTION

I. In General

Figure 2:
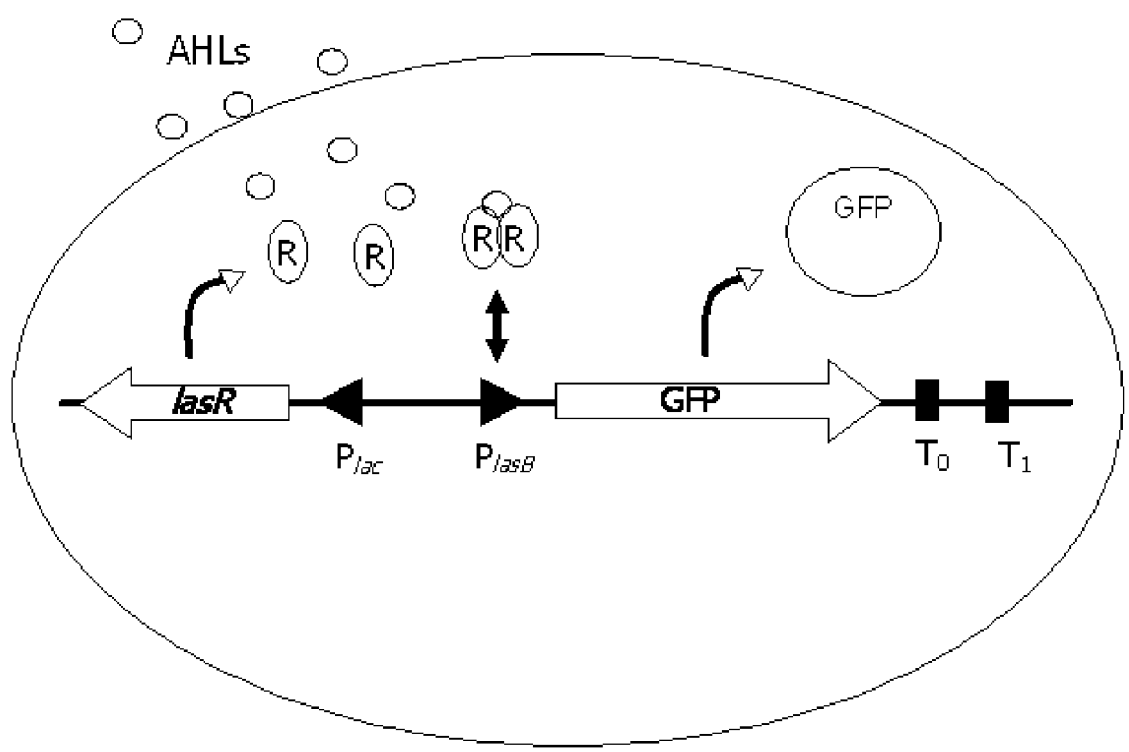
FIG. 2 is a schematic depiction of the green fluorescent protein (GFP) biosensor construct used to screen for Pseudomonas aeruginosa quorum sensing antagonists and agonists. When AHL was added, expression of GFP was induced (for details, see Hentzer et al., 2002, Microbiol. 148:87-102).
Figure 4:
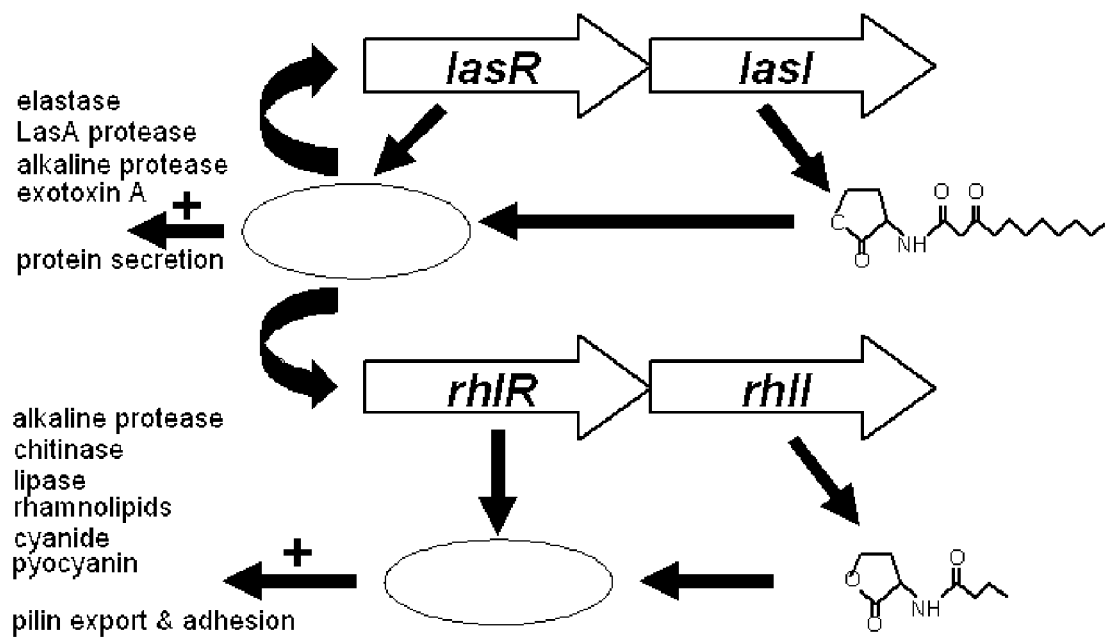
FIG. 4 shows the quorum sensing pathway of Pseudomonas aeruginosa.

Before the present methods are described, it is understood that this invention is not limited to the particular methodology, protocols, cell lines, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably.

As defined herein, "contacting" means that the quorum sensing compound used in the present invention is introduced into a sample containing the receptor in a test tube, flask, tissue culture, chip, array, plate, microplate, capillary, or the like, and incubated at a temperature and time sufficient to permit binding of the quorum sensing compound to a receptor. Methods for contacting the samples with the quorum sensing compound or other specific binding components are known to those skilled in the art and may be selected depending on the type of assay protocol to be run. Incubation methods are also standard and are known to those skilled in the art.

In another embodiment, the term "contacting" means that the quorum sensing compound used in the present invention is introduced into a subject receiving treatment, and the compound is allowed to come in contact in vivo.

As used herein, the term "treating" includes preventative as well as disorder remittent treatment. As used herein, the terms "reducing", "suppressing" and "inhibiting" have their commonly understood meaning of lessening or decreasing.

In certain embodiments, the present invention encompasses administering the compounds useful in the present invention to a patient or subject. A "patient" or "subject", used equivalently herein, refers to a plant or an animal. In particular, an animal refers to a mammal, preferably a human. The subject either: (1) has a pathogen remediable or treatable by administration of a quorum sensing compound; or (2) is susceptible to an pathogen that is preventable by administering a quorum sensing compound.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference for the purpose of describing and disclosing the chemicals, cell lines, vectors, animals, instruments, statistical analysis and methodologies which are reported in the publications which might be used in connection with the invention. Nothing herein is to be construed as an admission that the invention is not entitled to antedate such disclosure by virtue of prior invention.

II. The Invention

Many Gram negative bacteria use quorum sensing, an intercellular signaling network that relies on N-acyl homoserine lactone signal molecules (AHL), to regulate and coordinate behaviors and interactions. Expression of quorum sensing-regulated genes is contingent on a LuxR-type transcriptional regulator and the accumulation of a threshold concentration of the cognate AHL. The present invention generally identifies new tools to stimulate or disrupt quorum sensing for the study of communication in microbial communities. About 16,000 synthetic compounds were screened from a library for induction and inhibition of quorum sensing in a *Pseudomonas putida* AHL sensor strain, engineered with the LasR transcriptional activator, which controls virulence gene expression in *Pseudomonas aeruginosa*. LasR activity was monitored by measuring GFP (green fluorescent protein) expression from a transcriptional fusion between GFP and the promoter from lasB, which is under the control of LasR. The screen identified several novel compounds that inhibited expression of GFP in the AHL biosensor strain in the presence of exogenous AHL. The screen also identified novel inducers of LasR that do not share structural similarities to AHLs. These compounds appear to be specific for the LasR activator and do not affect quorum sensing-regulated gene expression in AHL sensor strains with different LuxR-type regulators. These results provide the groundwork for combining chemical diversity with gene regulation studies to dissect communication networks.

The present invention generally provides methods and compositions for modulating quorum sensing in a microbe. Specifically, the present invention provides compounds selectively modulating bacterial quorum sensing. Through inhibition of the quorum sensing system the expression of many virulence genes and other phenotypes like swarming motility and biofilm formation are significantly reduced or completely abolished rendering a bacterial population more susceptible to the host immune response or to treatment with traditional antibacterial agents.

In a preferred embodiment, the present invention provides a method for modulating quorum sensing of a bacterium. The method comprises contacting said bacterium with at least one quorum sensing compound selected from the group consisting of:

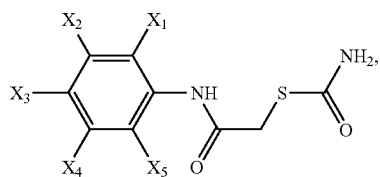

wherein $X_1$, $X_2$, $X_3$, $X_4$, and $X_5$ are independently selected from the group consisting of H, OH, F, Cl, Br, I, $OR_1$, $COOR_1$ and $R_1$, and wherein $R_1$ is $(CH)_nH$ and n is an integer between 0-5;

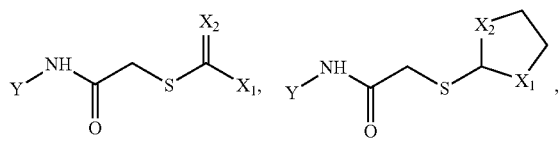

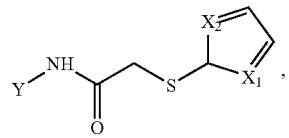

wherein $X_1$ is O, S, or N saturated with hydrogen atoms, $X_2$ is O, Y is selected from a group consisting of a heterocyclic aromatic ring having a nucleophilic group, an aromatic ring having a nucleophilic group, and

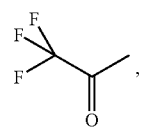

wherein the nucleophilic group is selected from the group consisting of OH, F, Cl, Br, I, OR, $COOR_1$ and $R_1$, wherein $R_1$ is $(CH)_nH$ and n is an integer between 0-5;

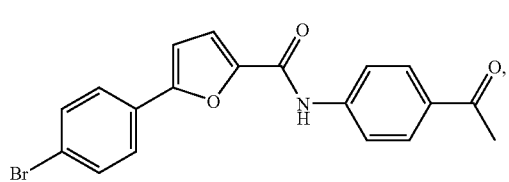

A12

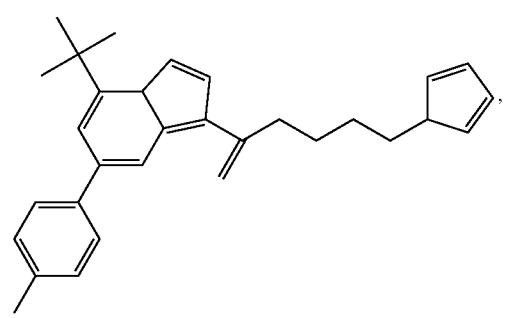

A10

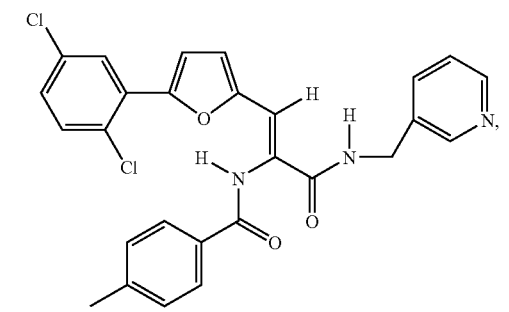

A9

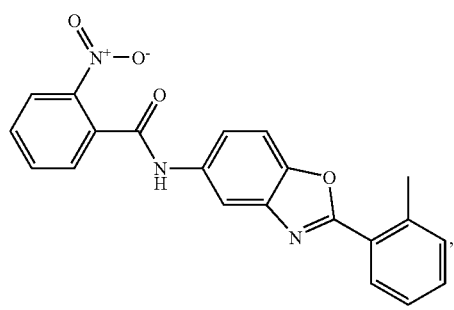 A14
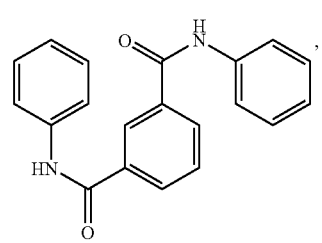 A7
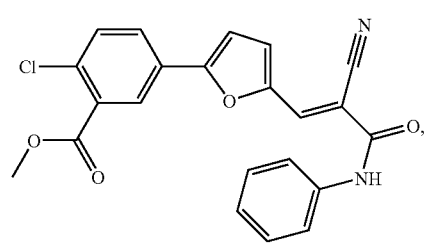 A4
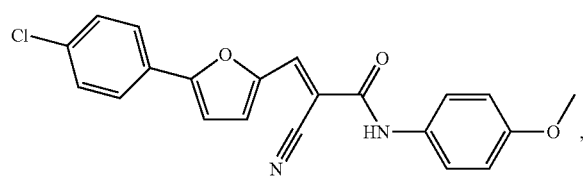 A2
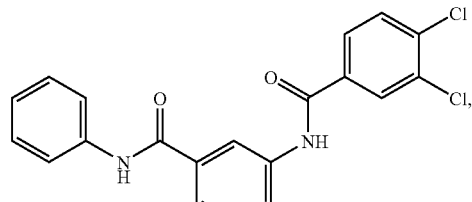 A11
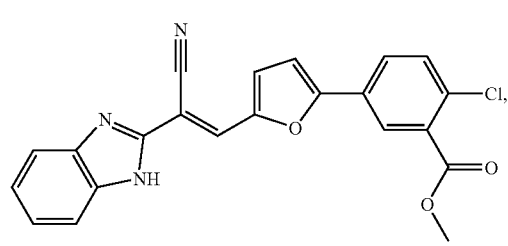 A5
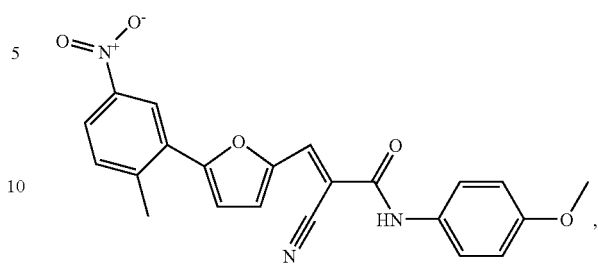 A3
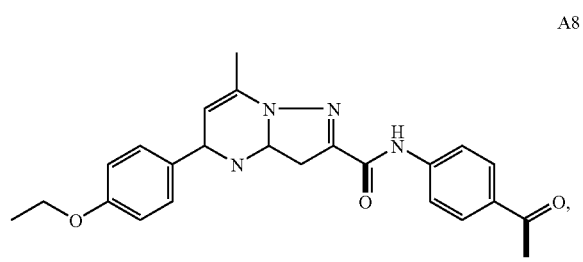 A8
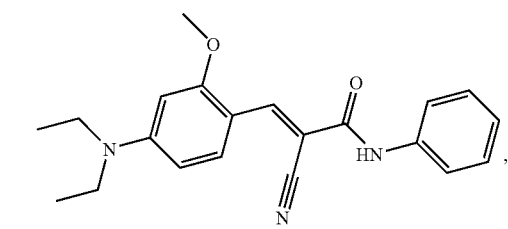 A1
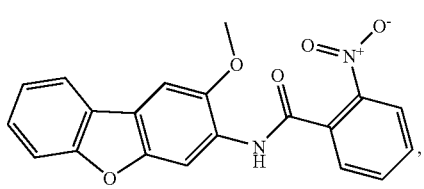 A6
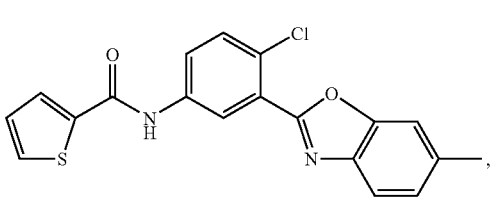 A13
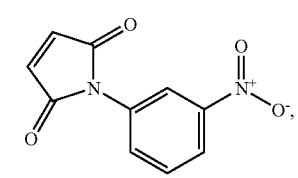 X2
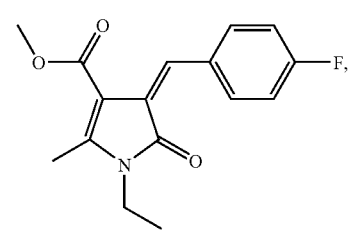 X8

-continued

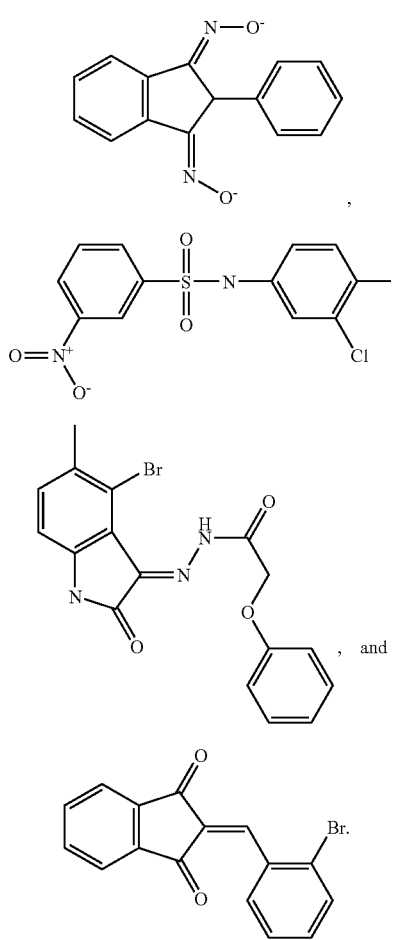

, and

In a preferred embodiment, the heterocyclic aromatic ring includes an aromatic 3 to 8 membered ring which has at least one hetero atom, such as, O, S, N, and O. The aromatic ring also includes a 3-8 membered ring. As described above, both the heterocyclic aromatic ring and the aromatic ring have preferably got strong electron withdrawing groups attached to the ring.

In this method the bacterium is *Pseudomonas aeruginosa*. The method further comprises contacting the bacterium with a suitable antibiotic. The suitable antibiotic may be selected from the group consisting of aminoglycosides, β-lactam antibiotics, and fluoroquinolones.

*Pseudomonas aeruginosa* is a human opportunistic pathogen, and is perhaps the best understood among bacteria that utilize HSL-based quorum sensing as part of their lifestyle, especially in terms of the role quorum sensing plays in pathogenicity. This pathogen causes hospital-transmitted, or nosocomial, infections in immunocompromised patients and has an extremely high potential to develop resistance mechanisms against traditional antibiotic treatment. It produces many virulence factors, including several proteases, exotoxin A, rhamnolipid, pyocyanin, cyanide and chitinase.

Pathogenicity is regulated by two interlinked quorum sensing circuits, and the quorum sensing signaling system is involved in the ability of *Pseudomonas aeruginosa* to form biofilms (Davies et al., 1998, Science 280:295-8). Recently, another human opportunistic pathogen, *Burkholderia cepacia*, Huber et al. (2001, Microbiol. 147:2517-28,) was demonstrated to depend on an HSL-based quorum sensing system for biofilm formation and swarming motility.

In another preferred embodiment, the present invention provides a method for modulating biofilm formation on a surface. This method comprises the step of administering a quorum sensing compound to the surface. As shown above, the quorum sensing compound is selected from the group consisting of:

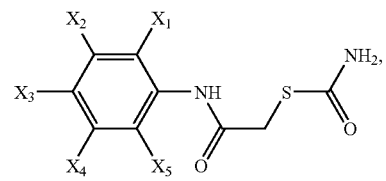

wherein $X_1$, $X_2$, $X_3$, $X_4$, and $X_5$ are independently selected from the group consisting of H, OH, F, Cl, Br, I, $OR_1$, $COOR_1$ and $R_1$, and wherein $R_1$ is $(CH)_nH$ and n is an integer between 0-5;

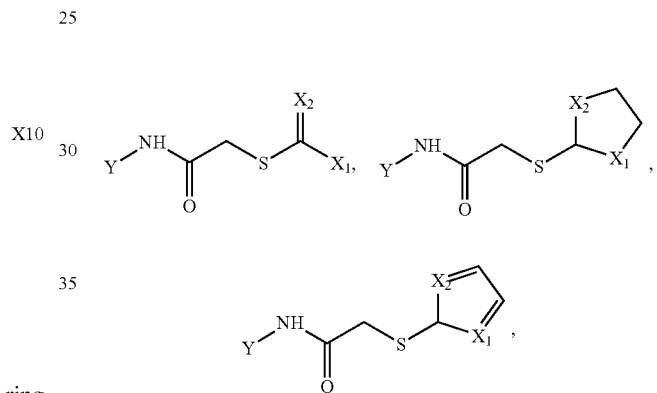

wherein X, is O, S, or N saturated with hydrogen atoms, $X_2$ is O, Y is selected from a group consisting of a heterocyclic aromatic ring having a nucleophilic group, an aromatic ring having a nucleophilic group, and

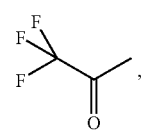

wherein the nucleophilic group is selected from the group consisting of OH, F, Cl, Br, I, OR, $COOR_1$ and $R_1$, wherein $R_1$ is $(CH)_nH$ and n is an integer between 0-5;

A12

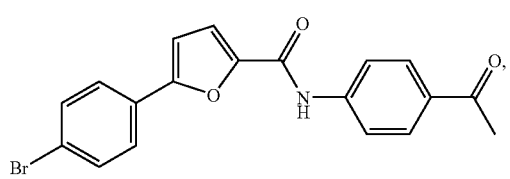

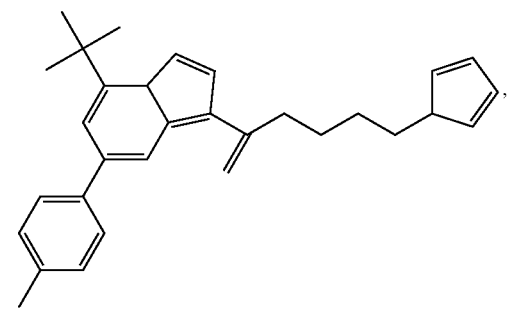
A10
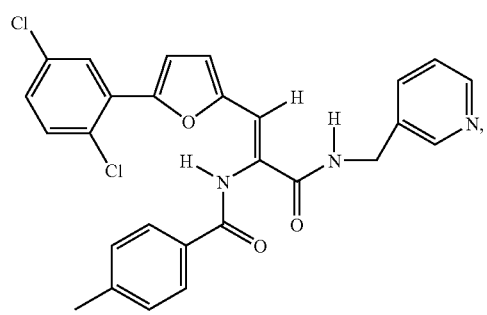
A9
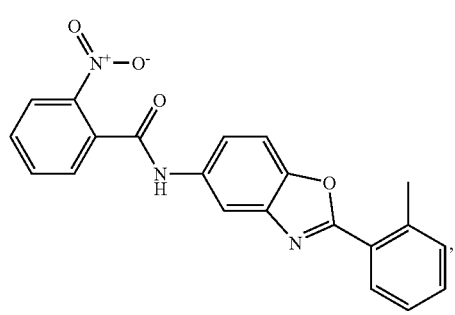
A14
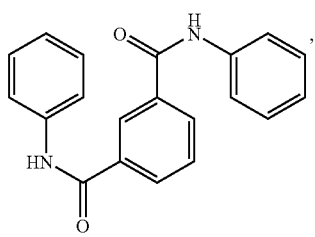
A7
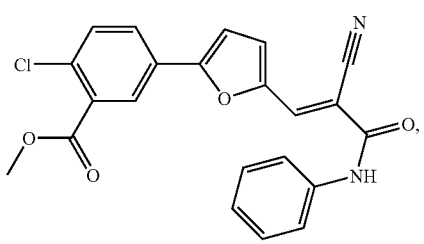
A4
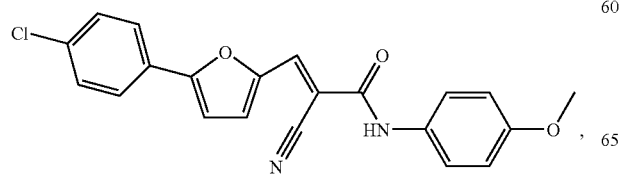
A2
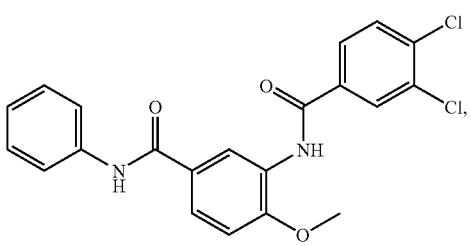
A11
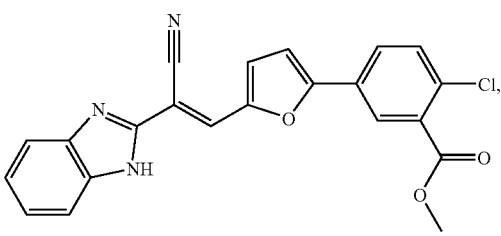
A5
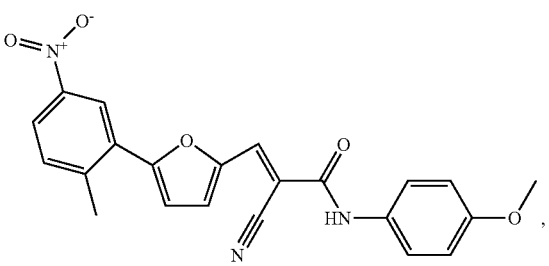
A3
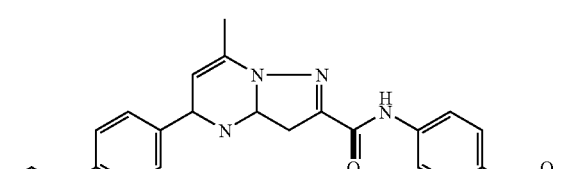
A8
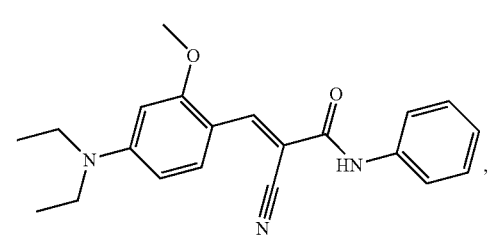
A1
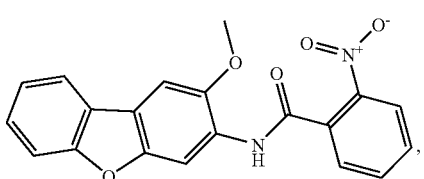
A6
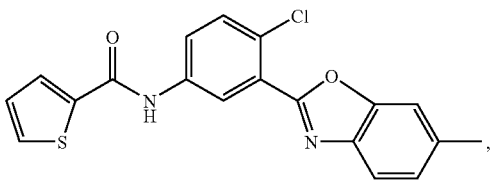
A13

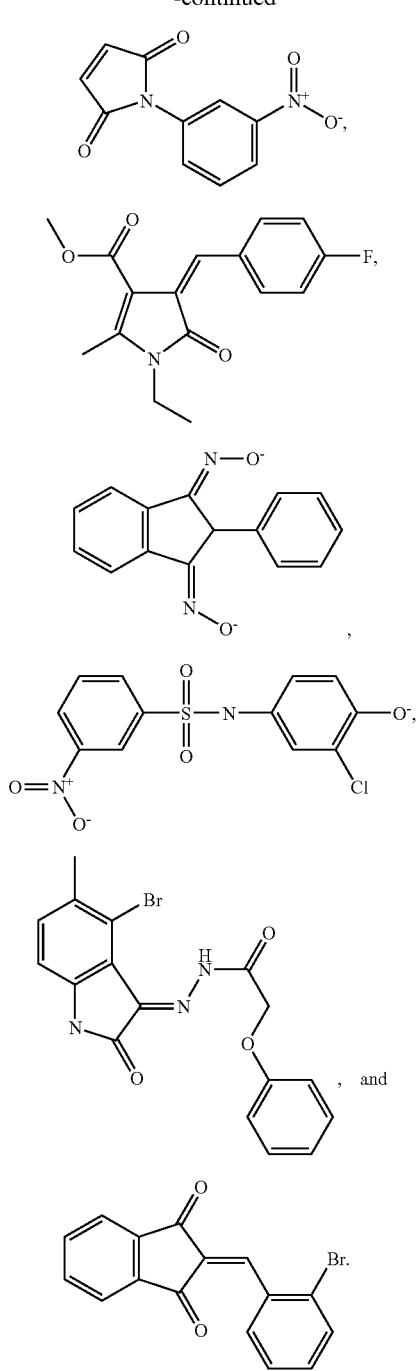

Biofilms are defined as an association of microorganisms (of the same or different species) growing attached to a surface and producing a slimy layer of extracellular polymers in which the microbial consortia are embedded in a protective environment (for a review see: Costerton et al., Ann. Rev. Microbiol. 49:711-45, 1995). Biofilms represent a severe problem as bacteria integrated in such a polymer matrix develop resistance to conventional antimicrobial agents. *Pseudomonas aeruginosa* cells, for example, growing in an alginate slime matrix have been demonstrated to be resistant to antibiotics (e.g., aminoglycosides, β-lactam antibiotics, fluoroquinolones) and disinfectants (Govan et al., 1996, Microbiol. Rev. 60:539-74, 1996).

In most natural, clinical and industrial settings bacteria are predominantly found in biofilms. Drinking water pipes, ship hulls, teeth or medical devices represent typical surfaces colonized by bacteria. On the one hand biofilms decrease the life time of materials through corrosive action in the industrial field, a process also referred to as "biofouling." Furthermore, microbial biofilms growing for example on ship hulls increase fuel consumption through enhanced frictional resistance and simultaneously reduce maneuverability. On the other hand two thirds of all bacterial infections in humans are associated with biofilms (Lewis, 2001, Antimicrob. Agents Chemother. 45:999-1007. *Pseudomonas aeruginosa*, for example, forms infectious biofilms on surfaces as diverse as cystic fibrosis lung tissue, contact lenses, and catheter tubes (Stickler et al., 1998, Appl. Environm. Microbiol. 64:3486-90).

Since biofilm formation is demonstrated to require an HSL signaling system, inhibition of quorum sensing systems would result in an impaired ability to form biofilms and therefore in an increased susceptibility to antibacterial treatment.

The present invention provides a method for controlling virulence of pathogenic organisms and rendering them avirulent by blocking the quorum sensing system using novel compounds that are antagonists to quorum-sensing.

In this regard, another embodiment of the present invention provides a method of reducing virulence in a microbe. This method comprises the step of contacting the microbe with a quorum sensing compound. As discussed before, the quorum sensing compound may be selected from the group consisting of:

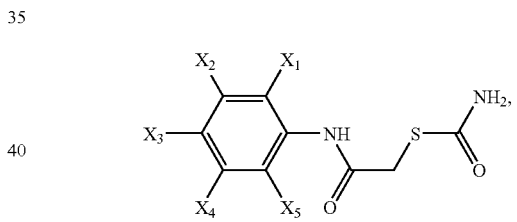

wherein $X_1$, $X_2$, $X_3$, $X_4$, and $X_5$ are independently selected from the group consisting of H, OH, F, Cl, Br, I, $OR_1$, $COOR_1$ and $R_1$, and wherein $R_1$ is $(CH)_nH$ and n is an integer between 0-5;

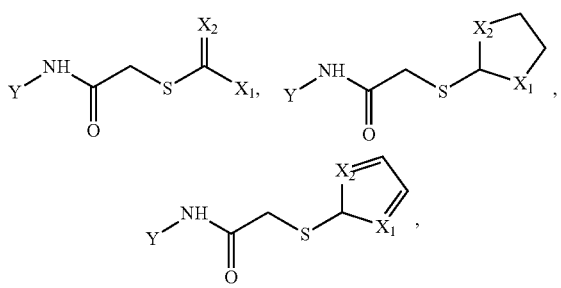

wherein $X_1$ is O, S, or N saturated with hydrogen atoms, $X_2$ is O, Y is selected from a group consisting of a heterocyclic aromatic ring having a nucleophilic group, an aromatic ring having a nucleophilic group, and wherein the nucleophilic group is selected from the group consisting of OH, F, Cl, Br, I, OR, COOR$_1$ and R$_1$, wherein R$_1$ is (CH)$_n$H and n is an integer between 0-5;

-continued

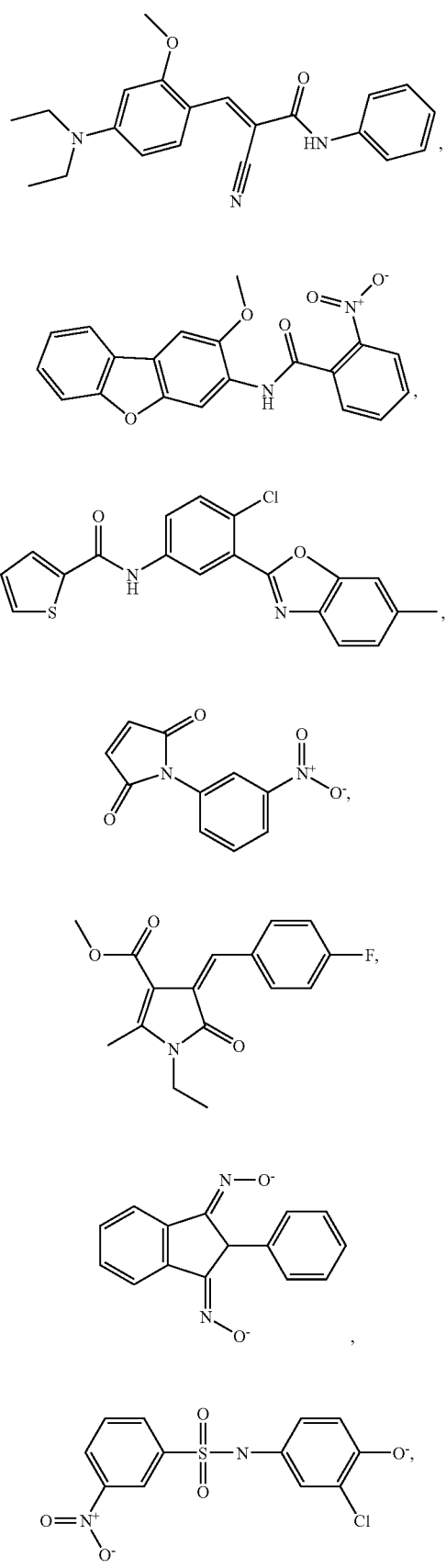

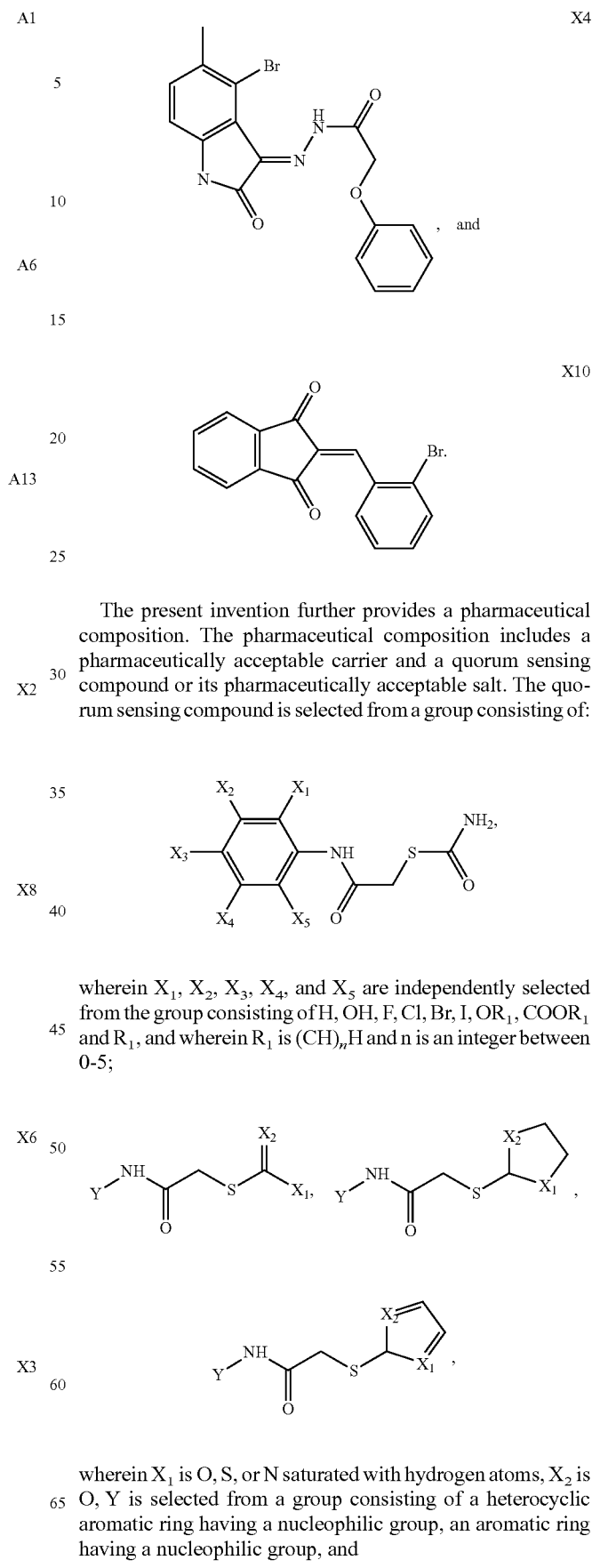

The present invention further provides a pharmaceutical composition. The pharmaceutical composition includes a pharmaceutically acceptable carrier and a quorum sensing compound or its pharmaceutically acceptable salt. The quorum sensing compound is selected from a group consisting of:

wherein $X_1$, $X_2$, $X_3$, $X_4$, and $X_5$ are independently selected from the group consisting of H, OH, F, Cl, Br, I, $OR_1$, $COOR_1$ and $R_1$, and wherein $R_1$ is $(CH)_nH$ and n is an integer between 0-5;

wherein $X_1$ is O, S, or N saturated with hydrogen atoms, $X_2$ is O, Y is selected from a group consisting of a heterocyclic aromatic ring having a nucleophilic group, an aromatic ring having a nucleophilic group, and

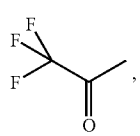
wherein the nucleophilic group is selected from the group consisting of OH, F, Cl, Br, I, OR, COOR$_1$ and R$_1$, wherein R$_1$ is (CH)$_n$H and n is an integer between 0-5;
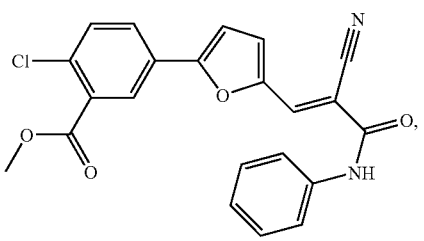
A4
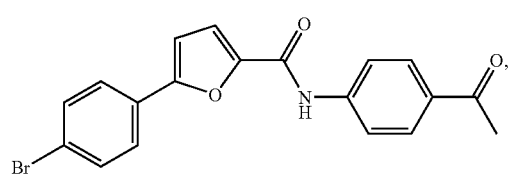
A12
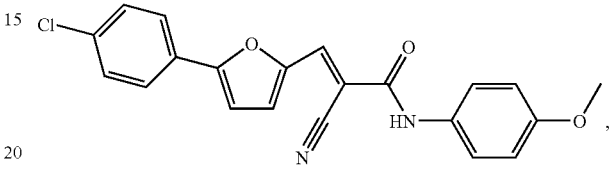
A2
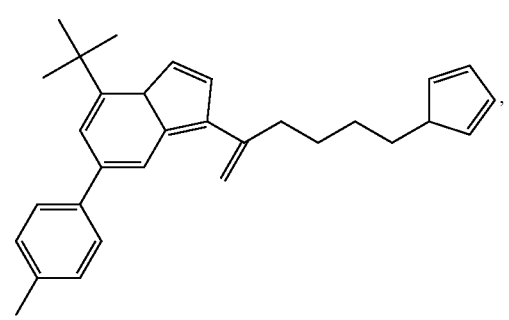
A10
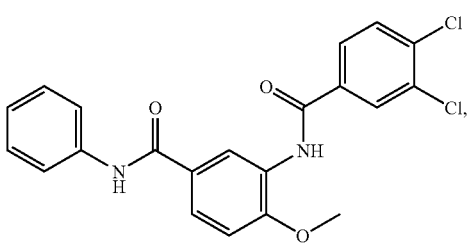
A11
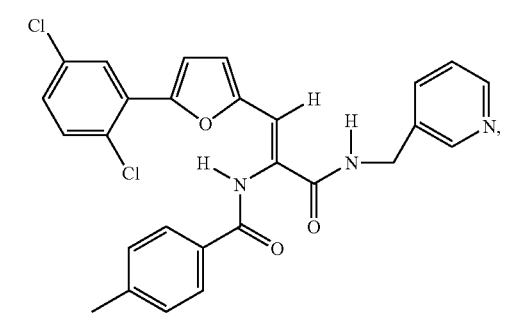
A9
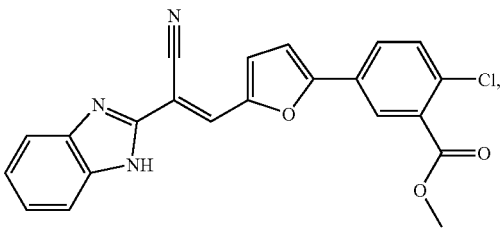
A5
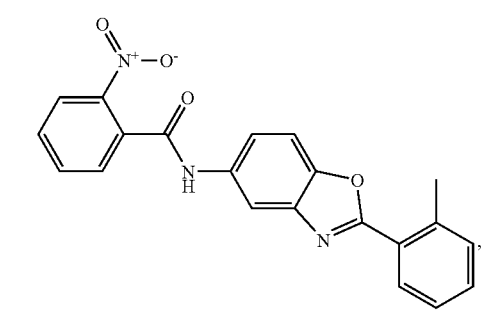
A14
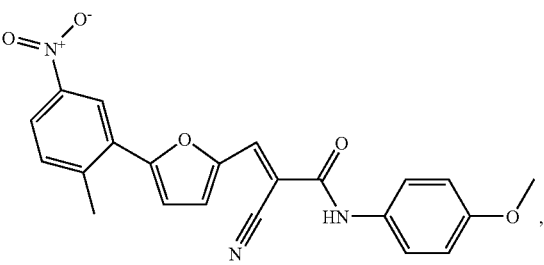
A3
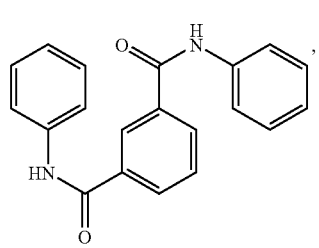
A7
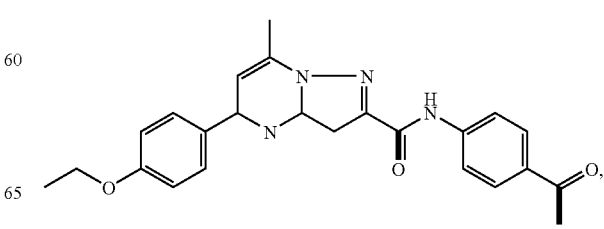
A8

A1

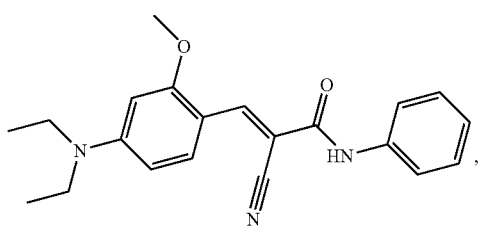

A6

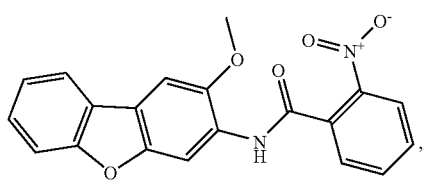

A13

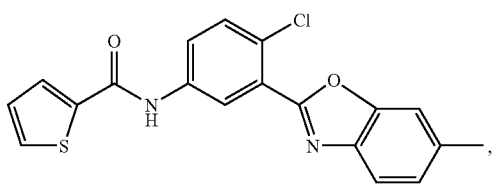

X2

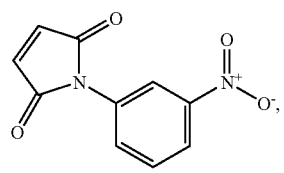

X8

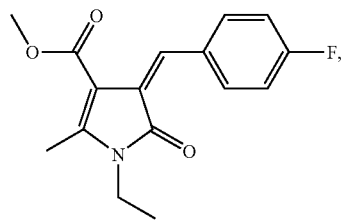

X6

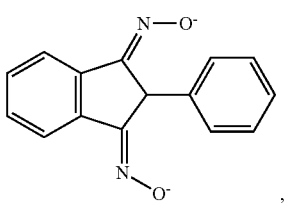

X3

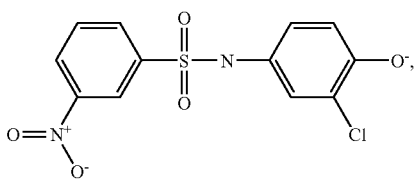

X4

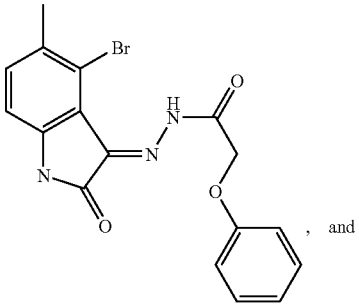, and

X10

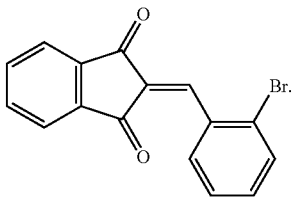

The pharmaceutical compositions may be used for instance as new antibiotic therapeutics, disinfectants, antifouling coatings or coatings of medical devices. In contrast to traditional antibacterial agents, the compounds of the present invention do not kill the microorganisms, but render them avirulent. The advantage of this strategy is that the emergence of bacterial resistance against such antimicrobials is significantly reduced.

In one embodiment, the compounds are useful for the treatment of a mammal, in particular human diseases caused by bacteria through the inhibition of the bacterial quorum sensing cascade rendering the pathogen avirulent. Such diseases include endocarditis, respiratory and pulmonary infections (preferably in immunocompromised and cystic fibrosis patients), bacteremia, central nervous system infections, ear infections including external otitis, eye infections, bone and joint infections., urinary tract infections, gastrointestinal infections and skin and soft tissue infections including wound infections, pyoderma and dermatitis which all can be triggered by *Pseudomonas aeruginosa*.

Furthermore, the compounds can be used for the treatment of pulmonary infections caused by *Burkholderia cepacia* (preferably in immunocompromised and cystic fibrosis patients), gastroenteritis and wound infections caused by *Aeromonas hydrophila*, sepsis in tropical and subtropical areas caused by *Chromobacterium violaceum*, diarrhoea with blood and haemolytic uremic syndrome (HUS) caused by *Escherichia coli*, yersiniosis triggered by *Yersinia enterocolitica* and *Y. pseudotuberculosis*, and transfusion-related sepsis and fistulous pyoderma caused by *Serratia liquefaciens*.

In another embodiment, the compounds can be used to prevent and/or treat plant diseases, where inhibition of the HSL-mediated signaling system reduces or abolishes virulence of bacterial plant pathogens. Such diseases include crown gall tumors caused by *Agrobacterium tumefaciens*, soft rot caused by *Burkholderia cepacia, Erwinia carotovora* and *E. chrysanthemi*, sweet corn and maize infections caused by *Pantoea stewartii* and wilt disease caused by *Ralstonia solanacearum*.

In a further embodiment, the compounds can be used for the prevention and/or treatment of animal diseases, preferably fish diseases such as septicemia caused by *Aeromonas hydrophila* and *Vibrio anguillarum*, furunculosis in salmonids caused by *Aeromonas salmonicida*, prawn infections caused by *Vibrio harveyi* and enteric redmouth disease caused by *Yersinia ruckeri*, but also for the prevention and/or treatment of insect diseases caused, for example, by *Xenorhabdus nematophilus*.

In a further embodiment, the present invention relates to a method of inhibiting and/or preventing medical device-associated bacterial infections. The invention provides articles coated and/or impregnated with an antagonist compound of the invention in order to inhibit and/or prevent biofilm formation thereon. The articles include surgical instruments, blood bag systems, permanently implanted devices such as artificial heart valve, prosthetic joint, voice prosthesis, stent, and shunt, or non-permanently implanted devices such as endotracheal or gastrointestinal tube, pacemaker, surgical pin or indwelling catheter.

The indwelling catheters include urinary catheters, vascular catheters, peritoneal dialysis catheter, central venous catheters and needleless connectors. The catheter materials can be polyvinylchloride, polyethylene, latex, teflon or similar polymeric materials, but preferably polyurethane and silicone or a mixture thereof. In order to reduce the risk of catheter-related bacterial infections, several catheters coated and/or impregnated with antiseptic or antimicrobial agents such as chlorhexidine/silver-sulfadiazine and minocycline/rifampin, respectively, have been developed. Nevertheless, the emerging risk of bacterial resistance against traditional antibiotics limits the routine use of antibiotic-coated catheters.

The compounds of the present invention, however, offer the possibility to effectively reduce catheter-related bacterial infections with a low risk of resistance development due to a novel therapeutic strategy targeting highly sensitive signal transduction mechanisms in bacteria. The preferred form of application is the coating and/or impregnating of catheter materials on both the inner and outer catheter surfaces. More preferably, the compounds of the present invention can be included in a mixture of antibacterial agents released continuously from a catheter-associated depot into the environment.

In a further embodiment, the compounds of the present invention and their pharmacologically acceptable salts can be administered directly to animals, preferably to mammals, and in particular to humans as antibiotics, as mixtures with one another or in the form of pharmaceutical preparations. The pharmaceutical compositions may be formulated to allow enteral or parenteral use, and may contain an effective dose of at least one of the antagonist or agonist compound of the invention, in addition to conventional pharmaceutical carriers and additives. The compounds can be administered in form of their salts, which are obtainable by reacting the respective compounds with physiologically acceptable acids and bases.

The therapeutics can be administered orally, e.g., in the form of pills, tablets, coated tablets, sugar coated tablets, lozenges, hard and soft gelatin capsules, solutions, syrups, emulsions or suspensions or as aerosol mixtures. Administration, however, can also be carried out rectally, e.g., in the form of suppositories, or parenterally, e.g., in the form of injections or infusions, or percutaneously, e.g., in the form of ointments, creams or tinctures.

As indicated above, the compounds of the present invention can be used alone, in combination with other compounds of this invention or in combination with other active compounds, for example with active ingredients already known for the treatment of the afore mentioned diseases, whereby in the latter case a favorable additive effect is noticed. In particular, a conventional antibiotic compound can be used with an antagonist or an agonist of the present invention, to achieve effective elimination of the pathogen.

The pharmaceutical preparations administerable by the invention can be prepared by known dissolving, mixing, granulating, or tablet-forming processes. For oral administration, the quorum sensing compounds or their physiologically tolerated derivatives such as salts, esters, N-oxides, and the like are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions. Examples of suitable inert vehicles are conventional tablet bases such as lactose, sucrose, or cornstarch in combination with binders such as acacia, cornstarch, gelatin, with disintegrating agents such as cornstarch, potato starch, alginic acid, or with a lubricant such as stearic acid or magnesium stearate.

Examples of suitable oily vehicles or solvents are vegetable or animal oils such as sunflower oil or fish-liver oil. Preparations can be effected both as dry and as wet granules. For parenteral administration (subcutaneous, intravenous, intraarterial, or intramuscular injection), the quorum sensing compounds or their physiologically tolerated derivatives such as salts, esters, N-oxides, and the like are converted into a solution, suspension, or expulsion, if desired with the substances customary and suitable for this purpose, for example, solubilizers or other auxiliaries. Examples are sterile liquids such as water and oils, with or without the addition of a surfactant and other pharmaceutically acceptable adjuvants. Illustrative oils are those of petroleum, animal, vegetable, or synthetic origin, for example, peanut oil, soybean oil, or mineral oil. In general, water, saline, aqueous dextrose and related sugar solutions, and glycols such as propylene glycols or polyethylene glycol are preferred liquid carriers, particularly for injectable solutions.

The present invention also provides a method for preventing transmission of bacterial pathogen in an object. This method comprises the step of administering a quorum sensing compound to the object. In this method, the quorum sensing compound is selected from a group consisting of:

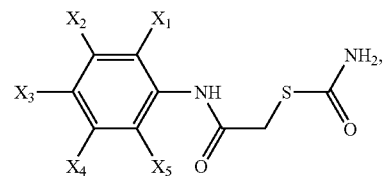

wherein $X_1$, $X_2$, $X_3$, $X_4$, and $X_5$ are independently selected from the group consisting of H, OH, F, Cl, Br, I, $OR_1$, $COOR_1$ and $R_1$, and wherein $R_1$ is $(CH)_nH$ and n is an integer between 0-5;

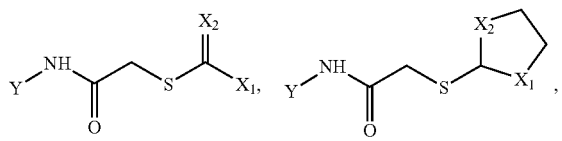

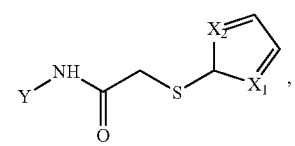

wherein $X_1$ is O, S, or N saturated with hydrogen atoms, $X_2$ is O, Y is selected from a group consisting of a heterocyclic aromatic ring having a nucleophilic group, an aromatic ring having a nucleophilic group, and

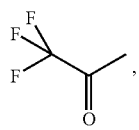

wherein the nucleophilic group is selected from the group consisting of OH, F, Cl, Br, I, OR, COOR$_1$ and R$_1$, wherein R$_1$ is $(CH)_nH$ and n is an integer between 0-5;

A12

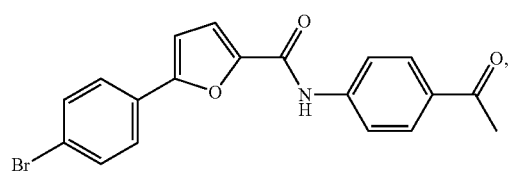

A10

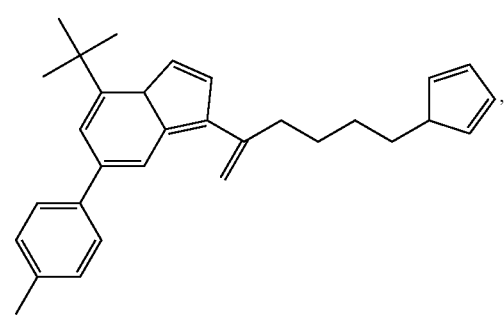

A9

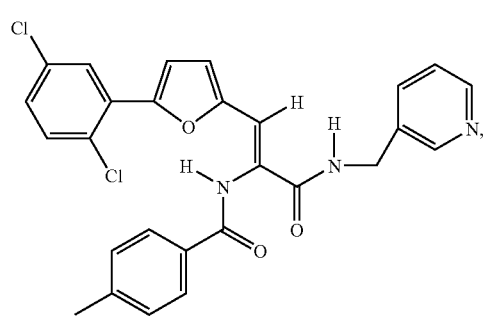

A14

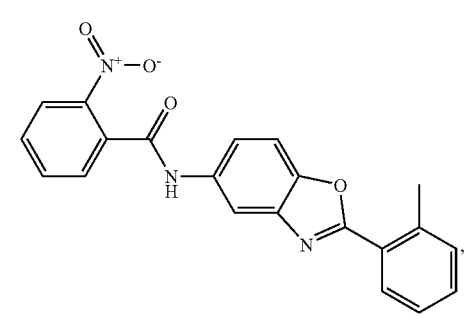

-continued

A7

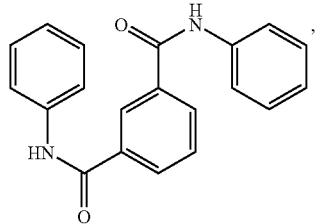

A4

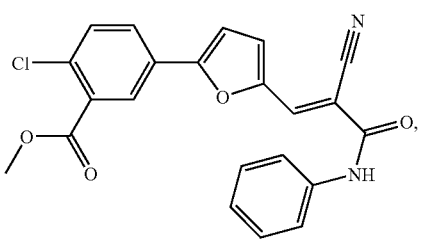

A2

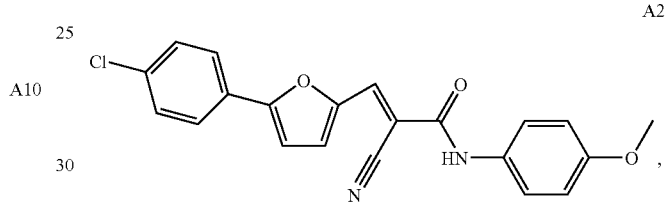

A11

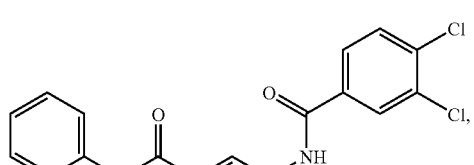

A5

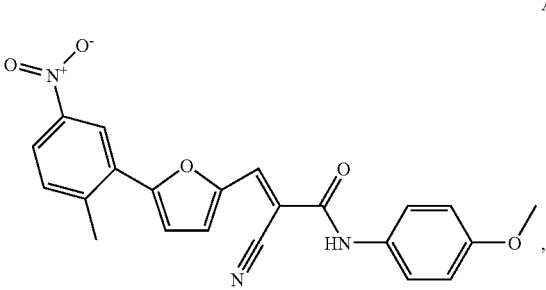

A3

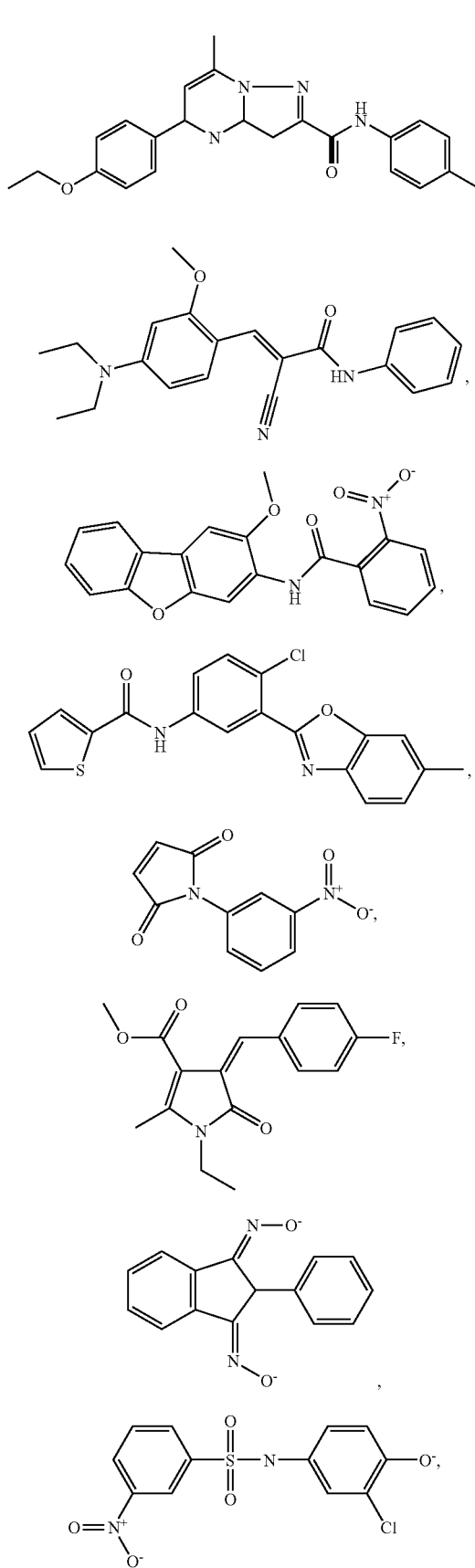
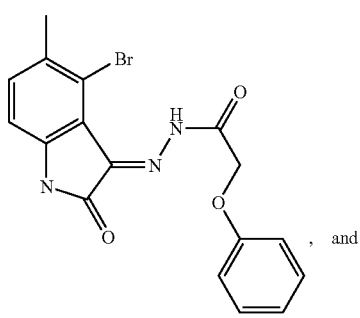

In this regard, the method is provided to remove, diminish, detach or disperse a bacterial biofilm from a living or nonliving surface by treating the surface with the antagonists of the present invention. This method is also useful to prevent biofilm formation on a living or nonliving surface by treating the surface with a compound of the present invention before bacterial colonization can initialize. The compounds of the present invention can be applied in a wide variety of different fields such as environmental, industrial and medical applications in order to prevent and/or treat damages or diseases caused by bacteria.

In one aspect, the compounds of the present invention can be used wherever it is beneficial to inhibit quorum sensing systems in order to prevent and/or treat colonization and biofilm formation. The compound is preferably applied to the surface as a solution of the compound, alone or together with other suitable materials such as conventional surfactants, or detergents, biocides, fungicides, antibiotics, pH regulators, perfumes, dyes or colorants. In combination with a bacteriocidal agent, the compounds of the present invention inhibit virulence or biofilm formation whilst the bacteriocidal agent kills the pathogens.

In yet another embodiment, the compounds can be used as antibacterial agent for topical use in cleaning and treatment solutions such as disinfectants, detergents, household cleaner and washing powder formulations in the form of a spray or a dispensable liquid. Preferably, these solutions can be applied to windows, floors, clothes, kitchen and bathroom surfaces and other surfaces in the area of food preparation and personal hygiene. In addition, the compounds can be used as antibacterial ingredients in personal hygiene articles, toiletries and cosmetics such as dentifrices, mouthwashes, soaps, shampoos, shower gels, ointments, creams, lotions, deodorants and disinfectants and storage solutions for contact lenses.

In another embodiment, the compounds can be used to prevent or treat bacterial biofilms in industrial settings such as ship hulls, paper manufacturing, oil recovery, food processing and other applications where biofouling on surfaces is a concern.

The compounds here can be used in form of a solution, paint or coating. The compounds can also be applied to water processing plants or drinking water distribution systems where the colonized surface (e.g., by *Pseudomonas aerugi-*

*nosa*) is the inside of an aqueous liquid system such as water pipes, water injection jets, heat exchangers and cooling towers.

Yet another embodiment of the present invention provides a method of regulating microbial disease resistance or susceptibility to a microbial disease in a subject. This method comprises the step of contacting said microbe with a quorum sensing compound of formula:

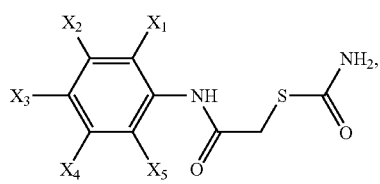

wherein $X_1$, $X_2$, $X_3$, $X_4$, and $X_5$ are independently selected from the group consisting of H, OH, F, Cl, Br, I, $OR_1$, $COOR_1$ and $R_1$, and wherein $R_1$ is $(CH)_nH$ and n is an integer between 0-5;

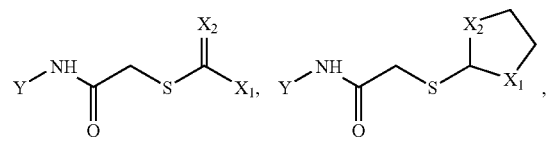

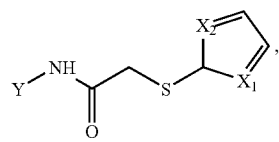

wherein $X_1$ is O, S, or N saturated with hydrogen atoms, $X_2$ is O, Y is selected from a group consisting of a heterocyclic aromatic ring having a nucleophilic group, an aromatic ring having a nucleophilic group, and

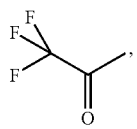

wherein the nucleophilic group is selected from the group consisting of OH, F, Cl, Br, I, OR, $COOR_1$ and $R_1$, wherein $R_1$ is $(CH)_nH$ and n is an integer between 0-5;

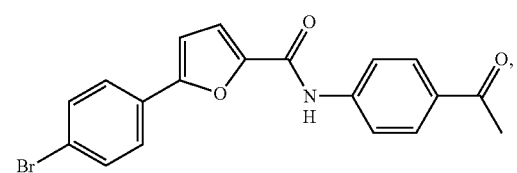
A12

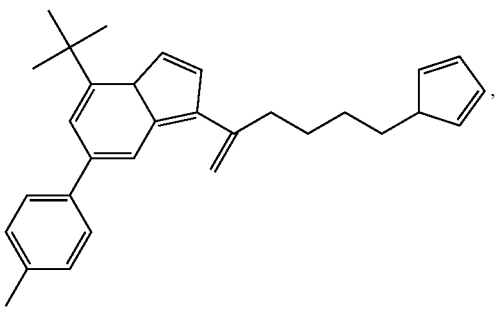
A10

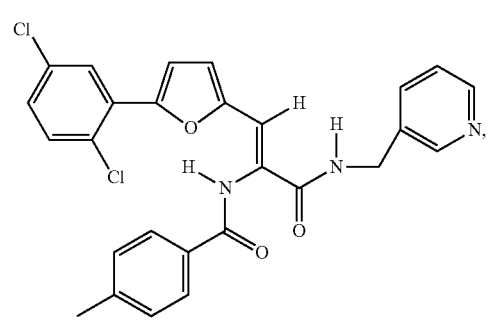
A9

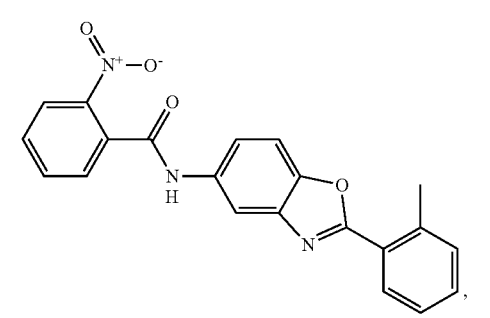
A14

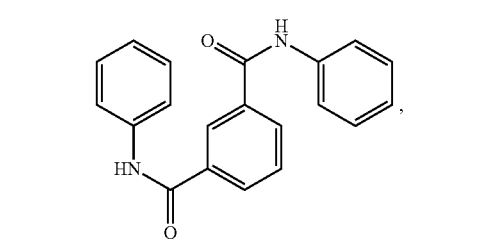
A7

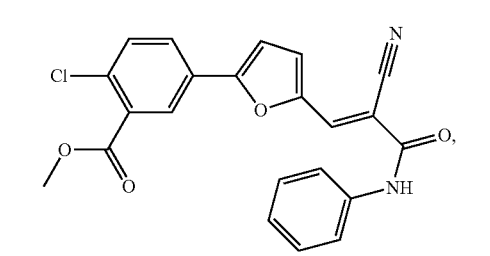
A4

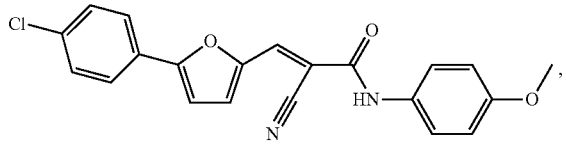
A2

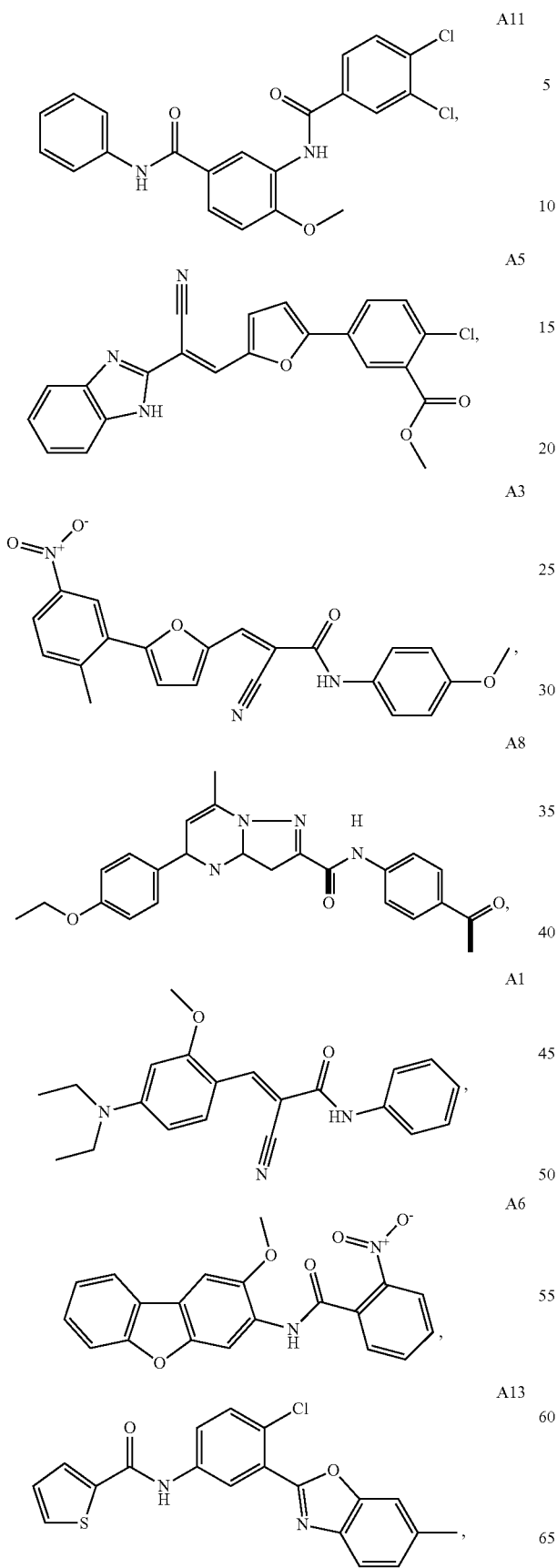
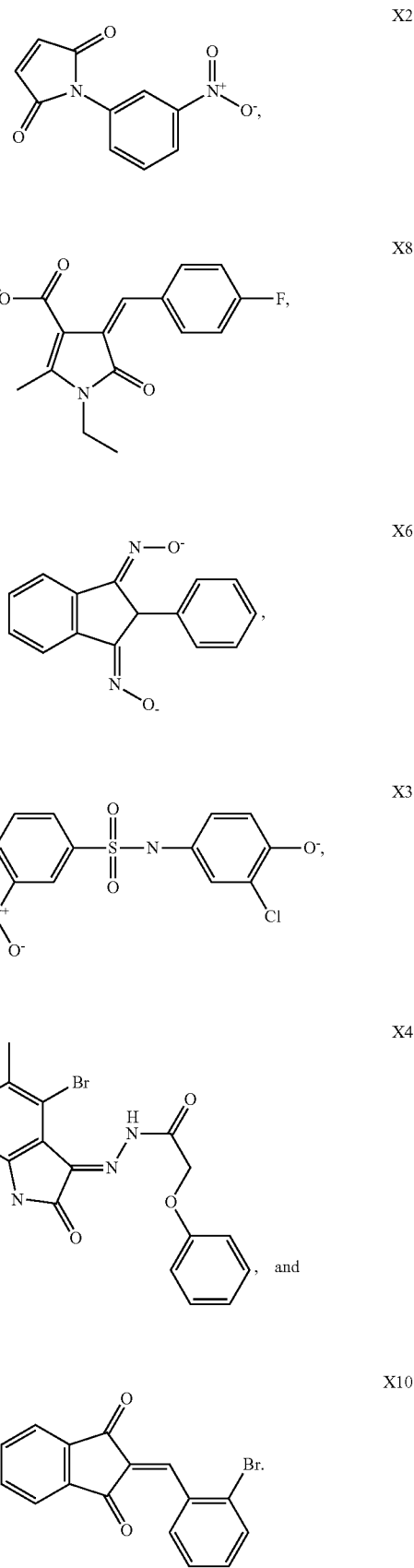

TABLE 1

| Structure | Formula | Mol Weight | Signal 671/672 | Signal 673/674 | Signal 674/875 | ID *indicates antagonist |
|---|---|---|---|---|---|---|
| (2-methoxyphenyl) | C₁₀H₁₂N₂O₃S | 240.2827 | 99128 | 169923 | 572429 | 5947535 |
| (2-hydroxyphenyl) | C₉H₁₀N₂O₃S | 226.2557 | 31966 | 33599 | 35234 | 5947920* |
| (4-bromophenyl) | C₉H₉BrN₂O₂S | 289.1523 | 99889 | 122318 | 382242 | 5948339 |
| (5-chloro-2-methylphenyl) | C₁₀H₁₁ClN₂O₂S | 258.7284 | 120140 | 98180 | 418594 | 5948544 |
| (4-methoxyphenyl) | C₁₀H₁₂N₂O₃S | 240.2827 | 580722 | 341731 | 1742777 | 5948690 |
| (3,4-dichlorophenyl) | C₉H₈Cl₂N₂O₂S | 279.1463 | 314238 | 171491 | 686157 | 5949527 |
| (2-bromophenyl) | C₉H₉BrN₂O₂S | 289.1523 | 184012 | 227644 | 1811011 | 5949674 |
| (3-fluorophenyl) | C₉H₉FN₂O₂S | 228.2467 | 100580 | 97648 | 265386 | 5949713 |
| (2,4-dimethoxyphenyl) | C₁₁H₁₄N₂O₄S | 270.3092 | 358647 | 332745 | 1769017 | 5950824 |

TABLE 1-continued

| Structure | Formula | Mol Weight | Signal 671/672 | Signal 673/674 | Signal 674/875 | ID *indicates antagonist |
|---|---|---|---|---|---|---|
| | $C_{11}H_{12}N_2O_4S$ | 268.2933 | 135505 | 176618 | 1041625 | 5951673 |
| | $C_{11}H_{12}N_2O_4S$ | 268.2933 | 161090 | 186369 | 1124336 | 5952057 |
| 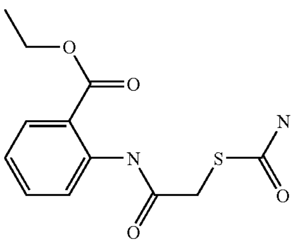 | $C_{12}H_{14}N_2O_4S$ | 282.3204 | 29681 | 31840 | 32358 | 5952120* |
| 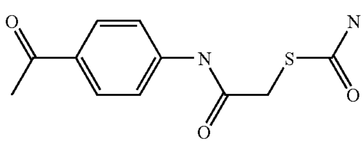 | $C_{11}H_{12}N_2O_3S$ | 252.2939 | 464145 | 594209 | 1805803 | 5952389 |
| 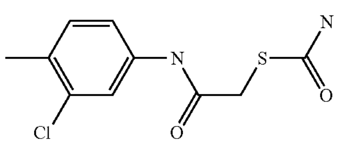 | $C_{10}H_{11}ClN_2O_2S$ | 258.7284 | 176752 | 223255 | 652341 | 5952472 |
| 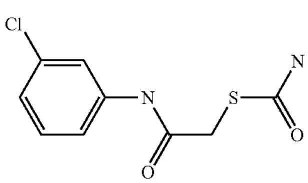 | $C_9H_9ClN_2O_2S$ | 244.7013 | 71274 | 87420 | 218815 | 5953997* |
| 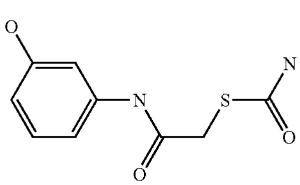 | $C_9H_{10}ClN_2O_3S$ | 226.2557 | 400739 | 298042 | 1565382 | 5955106 |
| 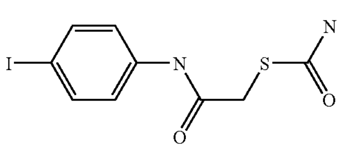 | $C_9H_9IN_2O_2S$ | 336.1527 | 375590 | 386242 | 1805793 | 5955203 |

TABLE 1-continued

| Structure | Formula | Mol Weight | Signal 671/672 | Signal 673/674 | Signal 674/875 | ID *indicates antagonist |
|---|---|---|---|---|---|---|
| (structure) | $C_{11}H_{14}N_2O_2S$ | 238.3104 | 120271 | 134098 | 694077 | 5955325 |
| (structure) | $C_{10}H_{12}N_2O_2S$ | 224.2833 | 266776 | 285870 | 1575457 | 5955821 |
| (structure) | $C_9H_9ClN_2O_2S$ | 244.7013 | 120221 | 145117 | 867440 | 5956488 |
| (structure) | $C_{11}H_{14}N_2O_2S$ | 238.3104 | 116987 | 131695 | 703195 | 5956611 |
| (structure) | $C_{10}H_{12}N_2O_3S$ | 240.2827 | 246680 | 243693 | 1277307 | 5956868 |

A screening system with green fluorescent protein as a reporter gene was adapted in a non-pathogenic species, Pseudomonas putida, closely related to Pseudomonas aeruginosa. A key element involved in the regulation of Pseudomonas aeruginosa, LasR, was engineered into the GFP construct (see FIG. 2), such that expression of GFP is linked to quorum sensing. Pseudomonas putida was then subjected to induction (e.g. by 3oxoC$_{12}$HsL or 3oxoC$_{10}$HsL) and/or inhibition by candidate chemical compounds from a commercially available combinatorial library. About 16,000 candidate compounds were individually screened.

The present invention provides both antagonists and agonists of bacterial quorum sensing. Both types of compound can be used for modulating bacterial quorum sensing. The novel antagonists and agonists of the present invention are structurally different from other, known antagonists and agonists, and the novel structures were unexpected because they were not predictable by modeling.

The present invention further provides agonist compounds that induce quorum sensing in bacteria, especially in Pseudomonas aeruginosa. The agonists of the present invention may be used to modulate bacterial quorum sensing. For example, the agonists compound of the present invention may induce premature switching of gene expression by a bacterial pathogen of virulence factors before the pathogen population reaches the critical mass. Because there is not enough pathogen cells, the virulence factors are not enough to cause symptoms or damages to the host, yet may induce sufficient host immune reactions, resulting in a resistance reaction and/or elimination of the pathogen. In addition, AHLs are broken down by Pseudomonas aeruginosa as an additional means of regulation. Agonists as described here would be resistant to degradation by Pseudomonas aeruginosa and could further alter pathogenesis.

The premature switching on of the virulence-related genes may further render the pathogen more susceptible to host immune reactions, or other antibiotic treatment.

Alternatively, quorum sensing agonists of the present invention may be used to increase virulence for biocontrol agents. For example, bacterial agents used to control weeds or insect pests may be induced to exhibit virulent reaction in a controllable manner for effective killing of the pests. Such precise control (e.g. by timing) may allow the pests to be killed with no or minimum collateral damage to the crop.

Because the agonists of the present invention are potent inducers of gene expression, they can further be used in combination with a suitable genetic construct for effective and precise induction of gene expression. For example, a recombinant expression vector may be constructed such that the desired gene to be expressed is under the control of a regulatory sequence (e.g. the lasB promoter under the transcriptional control of LasR) that is responsive to the agonist activities of the agonists of the present invention. This induction methodology is particularly suitable in eukaryotes, because the quorum sensing mechanism is unique to prokaryotic organisms and the agonists of the present invention are unlikely to induce non-specifically expression of other genes in a eukaryotic organism. This method of induction can be used in inducing gene expression in a fermentation production process of a recombinant protein product. Preferably, the method of inducing gene expression using the agonists of the present invention is used in gene therapy, wherein a genetic construct is delivered to a site of a patient in need thereof, and the expression of the gene(s) is specifically targeted and precisely timed or otherwise controlled by an additional administration of a suitable agonist of the present invention to the site. The gene expression may be further controlled by administering an antagonist of the present invention which will turn off the express of the gene contained in the construct.

The present invention further provides following examples of preferred methodologies, techniques and embodiments of the present invention. These are for illustrative purposes only and should not be deemed as narrowing the scope of the present invention.

EXAMPLE 1

Screen for Compounds that Act as Antagonists or Agonists of Quorum Sensing

Identification of Antagonists

Figure 10:
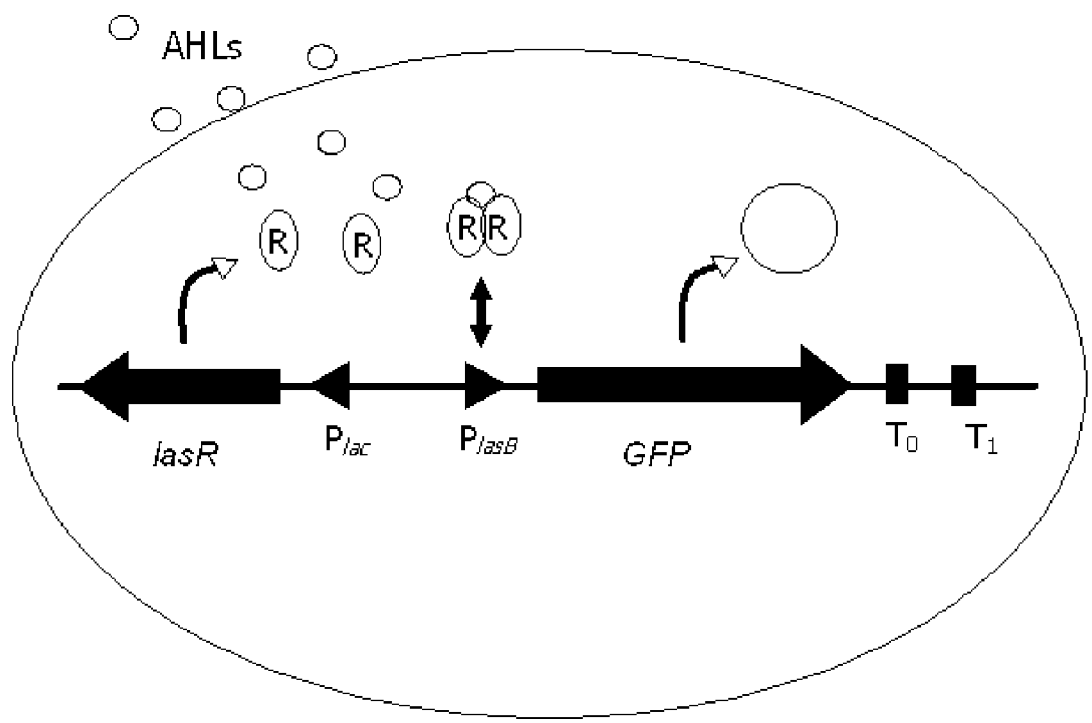
FIG. 10 depicts schematic monitoring of AHL-mediated communication.

Many Gram negative bacteria use quorum sensing, an intercellular signaling network that relies on N-acyl homoserine lactone signal molecules (AHL), to regulate and coordinate behaviors and interactions. Expression of quorum sensing-regulated genes is contingent on a LuxR-type transcriptional regulator and the accumulation of a threshold concentration of the cognate AHL. The experiments in this example relate to screening assays carried out to identify compounds that interfere with virulence gene expression under the control of the LasR transcriptional activator, a member of the LuxR family of transcriptional regulators. The inventors screened a library of approximately 16,000 synthetic compounds for induction and inhibition of quorum sensing in a *Pseudomonas putida* AHL sensor strain, engineered with the LasR transcriptional activator, which controls virulence gene expression in *Pseudomonas aeruginosa*. LasR mediated gene expression was monitored by measuring green fluorescent protein (GFP) expression from a transcriptional fusion between GFP and the promoter from lasB, which is under the control of LasR. lasB is a virulence gene that encodes an elastase involved in pathogenesis. A schematic illustration of the construct used in the screen is provided in FIGS. 2 and 10.

The initial screen utilized 3oxoC10HSL [N-(3-oxo-decanoyl)-L-homoserine lactone] as the inducer of LasR mediated signaling to identify compounds that compete with 3oxoC10HSL for half-maximal activation of GFP expression by the AHL reporter. This strategy enables identification of agonists and antagonists of LasR by pursuing compounds that either reduce or augment the activity of the AHL. The inventors further analyzed the antagonists in competition with 3oxoC12HSL [N-(3-oxo-dodecanoyl)-L-homoserine lactone]. The activities of the agonists were further characterized in the absence of AHL.

Initial Screen

To determine the effects of compounds on AHL-mediated quorum sensing, the reporter strain *P. putida* F117 pKRC12 was grown overnight at 28° C. in LB media, diluted with LB media to achieve an optical density of 0.05 at 600 nm (OD600), and 28 µl aliquots of cells were added to 384-well plates. 16,000 compounds were screened from a subset of the Chembridge DIVERSet, each at a final concentration of 100 nM. Bacterial cells at a final volume of 30 µl were incubated with the compounds for approximately 30 minutes prior to the addition of 3oxoC10HSL, at a final concentration of 100 nM. All of the compounds were dissolved in DMSO. DMSO was included in all controls. A Biomek FX liquid handler was used to dispense the reagents and bacteria into the 384-well plates. The initial screen was performed at room temperature. Fluorescence was measured at regular intervals after 3 hours using the EnVision plate reader (Perkin Elmer, inc.) with an excitation wavelength of 485 nm and emission detection at 510 nm. Compounds that reduced or increased the expression of GFP by a factor of greater than or equal three standard deviations from the mean values for controls containing 3oxoC10HSL were chosen for further analysis. Compounds that increased the expression of GFP by three standard deviations were designated as putative agonists. Compounds that decreased the expression of GFP by three standard deviations were designated as putative antagonists.

Figure 11:
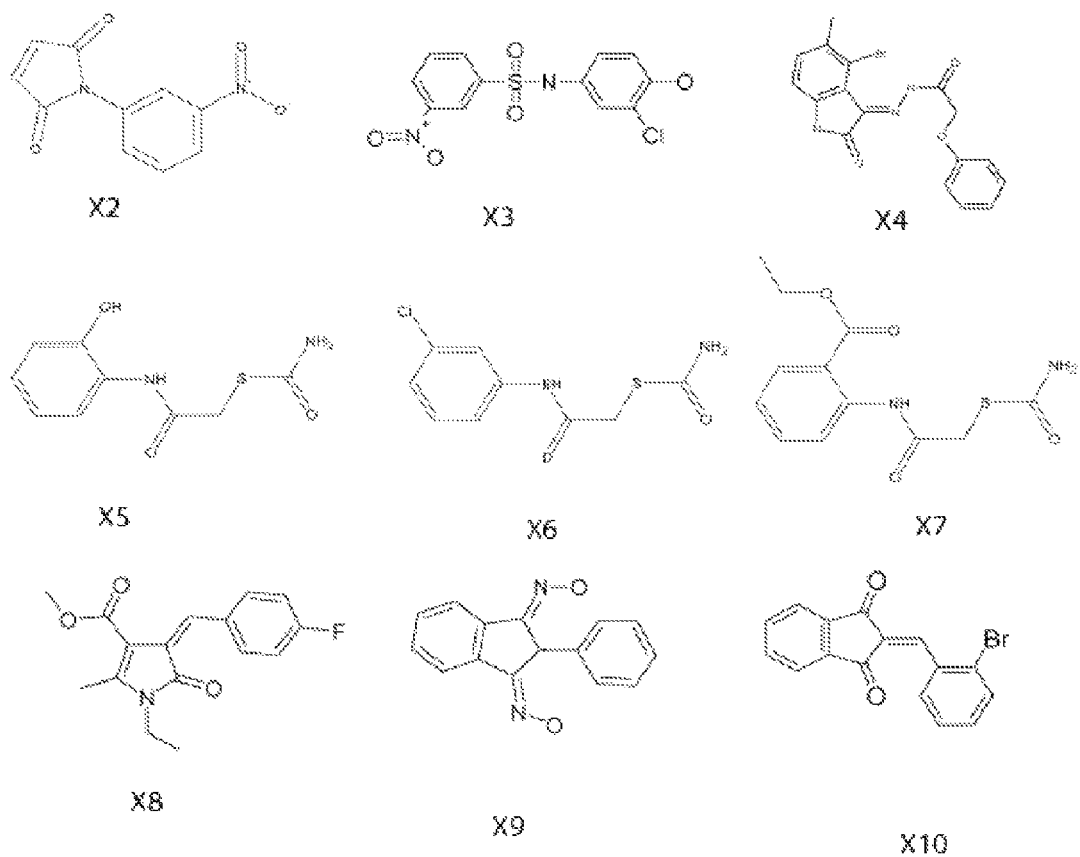
FIG. 11 depicts structures of Antagonists compounds identified in the primary screen.

Table 2 presents a list of the Chembridge and antagonist/agonist numerical designations. Please see FIG. 17 for chemical nomenclature of selected compounds from this library. FIGS. 5 and 11 present the structures of the antagonist compounds identified in this study.

TABLE 2

| Agonist designation = Chembridge number |
|---|
| A1 = 5881861 |
| A2 = 5878890 |
| A3 = 5866902 |
| A4 = 5884492 |
| A5 = 5883374 |
| A6 = 5802569 |
| A7 = 5180207 |
| A8 = 6074181 |
| A9 = 6239730 |
| A10 = 5847828 |
| A11 = 5724068 |
| A12 = 6024883 |
| A13 = 6030543 |
| Antagonist designation = Chembridge number |
| X2 = 5133201 |
| X3 = 5854800 |
| X4 = 5214835 |
| X5 = 5947920 |
| X6 = 5953997 |
| X7 = 5952120 |
| X8 = 6240194 |
| X9 = 5174514 |
| X10 = 5117815 |

Additional screens were performed as described above, except fluorescence was measured using the Wallac Victor2 plate reader with an excitation wavelength of 485 nm and emission detection at 515 nm. *E. coli* reporter induction assays were performed as described for *P. putida*. *Chromobacterium violaceum* CV026 and *Agrobacterium tumefaciens* KYC55 induction assays were performed by applying compounds to a lawn of bacteria on agar plates. *C. violaceum* CV026 inhibition assays were performed by applying compounds to a lawn of bacteria on agar plates containing synthetic N-3-oxohexanoyl-L-homoserine lactone.

Secondary Screens

Figure 6A:
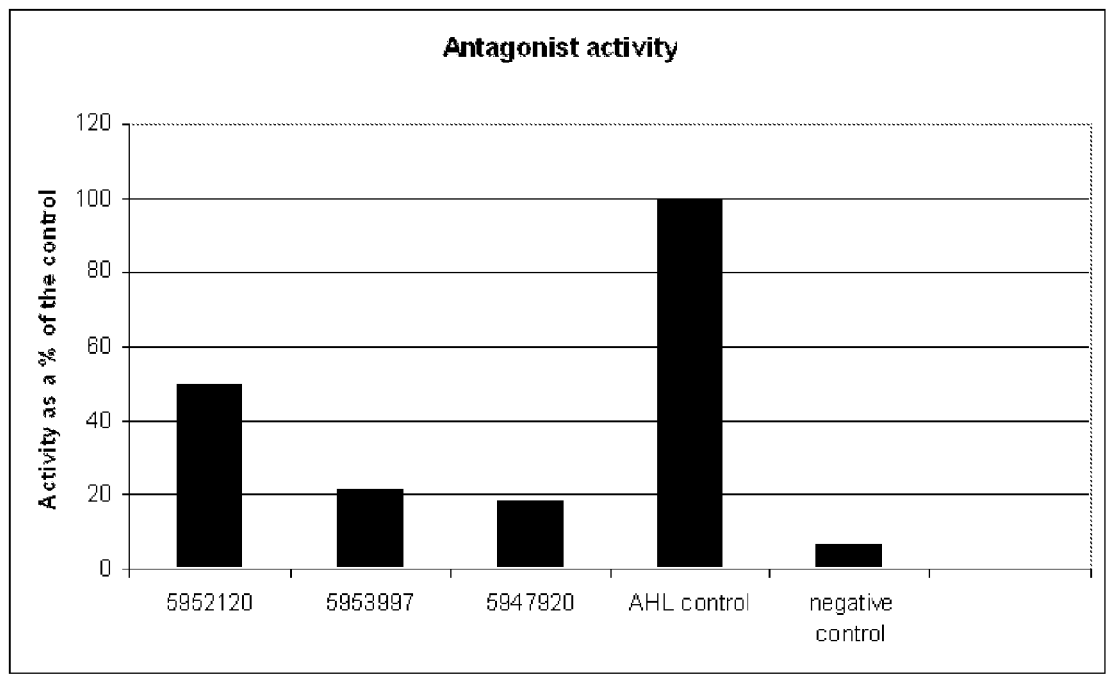
FIGS. 6a and 6b show that the antagonists inhibit quorum sensing related gene expression as measured by GFP activity as a percentage of the AHL control.
Figure 6B:
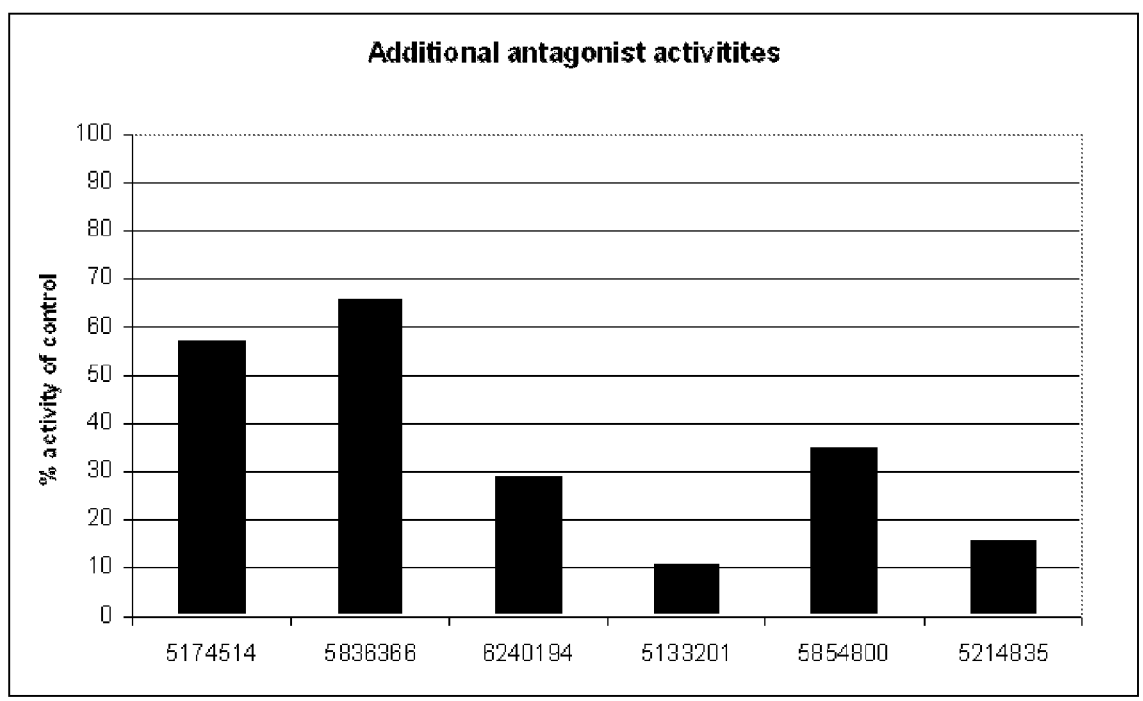

Additional screens were performed similar to screen described in the initial screen, except assays were performed in 96-well microtiter plates at a total volume of 100 μl. The reporter strain *P. putida* F117 pKRC12 was grown overnight at 28° C. in LB media, diluted with LB media to achieve an optical density of 0.05 at 600 nm (OD600), and 96 μl of cells were aliquoted to 96-well plates. Compounds were added at a final concentration of 100 nm or as otherwise indicated in each experiment and the bacterial cells were incubated with the compounds for approximately 30 minutes prior to the addition of 3oxoC10HSL or 3oxoC12HSL at a final concentration of 100 nM and 50 nM respectively or as indicated for each experiment. Fluorescence was measured at regular intervals after 3 hours using the Wallac Victor2 plate reader with an excitation wavelength of 485 nm and emission detection at 515 nm. Representative results are presented in FIGS. 6A and B and present the percentage of GFP expression activity as a function of expression of the AHL (3oxoC10 HSL) control. The numbers on the X axis refer to the Chembridge library reference number. Effects on growth of the antagonists were determined by measuring the optical density at 600 nm of growing bacterial cultures *P. putida* F 117 pKRC 12. Compounds did not impact the growth of the strain at concentrations of 10 μM. (Reference for *P. putida* F117 pKRC12: Steidle, A., K. Sigl, R. Schuhegger, A. Ihring, M. Schmid, S. Gantner, M. Stoffels, K. Riedel, M. Givskov, A. Hartmann, C. Langebartels, and L. Eberl. 2001. Visualization of N-acylhomoserine lactone-mediated cell-cell communication between bacteria colonizing the tomato rhizosphere. Appl Environ Microbiol 67:5761-70).

*E. coli* reporter assays were performed in 96-well microtiter plates at a total volume of 100 μl. The reporter strains *E. coli* DH10B pKRC12, *E coli* DH10B pJBA132, and *E. coli* MT102 pJBA132 were grown overnight at 37° C. in LB media, diluted with LB media to achieve an optical density of 0.05 at 600 nm (OD600), and 96 μl of cells were added to 96-well plates. Compounds were added at various concentrations as indicated in each experiment and the bacterial cells were incubated with the compounds for approximately 30 minutes prior to the addition of 3oxoC10HSL at a final concentration of 100 nM. Fluorescence was measured at regular intervals after 3 hours using the Wallac Victor2 plate reader with an excitation wavelength of 485 nm and emission detection at 515 nm. Representative results are presented in Table 3 and indicate the activity of the agonists or antagonists as activating gene expression in the absence of AHL or interfering with the gene expression when exogenous AHL is added. Plasmid pJBA132 is an artificial construct that contains the LuxR transcriptional activator under constitutive expression and GFP fused to luxI promoter. Regulation of the luxI promoter is under the control of the LuxR transcriptional activator. (Reference for *E coli* MT102 pJBA132: Andersen, J. B., A. Heydorn, M. Hentzer, L. Eberl, O. Geisenberger, B. B. Christensen, S. Molin, and M. Givskov. 2001. gfp-based N-acyl homoserine-lactone sensor systems for detection of bacterial communication. Appl Environ Microbiol 67:575-85.)

The reporter strains *E. coli* DH10B pKRC12 and *E. coli* DH10B pJBA132 were constructed by plasmid purification of pKRC12 and pJBA132 from *P. putida* F117 pKRC12 and *E. coli* MT102 pJBA132, followed by electroporation into electrocompetent *E. coli* DH10B.

*Chromobacterium violaceum* CV026 is a mutant that is unable to produce AHLs. Exogenous AHLs must be added to induce the LuxR-type transcriptional regulator which is designated CviR in this strain. Activation of CviR is indicated by the production of violacein. Cultures were grown overnight at 28° C. in LB media. Inhibition assays to determine the activity of the antagonists were conducted by spreading 100 μl of the overnight culture to create a lawn of bacteria on LB agar plates containing a final concentration 5 μM 3oxoC6HSL [N-(3-oxohexanoyl)-L-homoserine lactone]. 5 μl of 1 mM antagonists were spotted to the bacterial lawn. Inhibition of quorum sensing was qualitatively measured by observing the lack of production of violacein in areas where compounds were applied. Activation of quorum sensing by agonists was assayed similar to the antagonists, except that 3oxoC6HSL was excluded from the media. Activation of quorum sensing was qualitatively measured by observing the production of violacein in areas where compounds were applied. Representative results are presented in Table 3. The agonists and antagonists neither activated nor inhibited respectively in this assay. Controls consisting of 1 μl of 0.1 mg/ml of 3oxoC6HSL were spotted to the plates as a control and activated gene expression resulting in the production of a purple zone of violacein. (Reference for *C. violaceum* CV026: McClean, K. H., M. K. Winson, L. Fish, A. Taylor, S. R. Chhabra, M. Camara, M. Daykin, J. H. Lamb, S. Swift, B. W. Bycroft, G. S. Stewart, and P. Williams. 1997. Quorum sensing and *Chromobacterium violaceum*: exploitation of violacein production and inhibition for the detection of N-acylhomoserine lactones. Microbiology 143 (Pt 12):3703-11.)

*Agrobacterium tumefaciens* KYC55 is a mutant strain that is unable to produce AHLs. Exogenous AHLs must be added to induce the LuxR-type transcriptional regulator which is designated TraR in this strain. This strain contains a plasmid that encodes β-Galactosidase under the transcriptional control of TraR. Activation of TraR is indicated by the production of β-Galactosidase. Cultures were grown overnight at 28° C. in AMA broth. Induction assays were performed by applying compounds to a lawn of bacteria on AMA agar plates containing 40 mg of X-Gal per ml. 5 μl of 1 mM agonists were spotted to the bacterial lawn. Activation of quorum sensing was qualitatively measured by observing the production the blue pigment that results from β-Galactosidase cleavage of the X-gal substrate in areas where compounds were applied. Representative results are presented in Table 3. Agonists failed to induce β-Galactosidase activity in this assay. Controls consisting of 1 μl of 0.1 mg/ml of 3oxoC6HSL were spotted to the plates as a control and activated gene expression resulting in the production of β-Galactosidase and the formation of a blue zone. (Reference *A. tumefaciens* KYC55: Zhu, J., Y. Chai, Z. Zhong, S. Li, and S. C. Winans. 2003. Agrobacterium bioassay strain for ultrasensitive detection of N-acylhomoserine lactone-type quorum-sensing molecules: detection of autoinducers in *Mesorhizobium huakuii*. Appl Environ Microbiol 69:6949-53.

Characterization of Agonists

Figure 7:
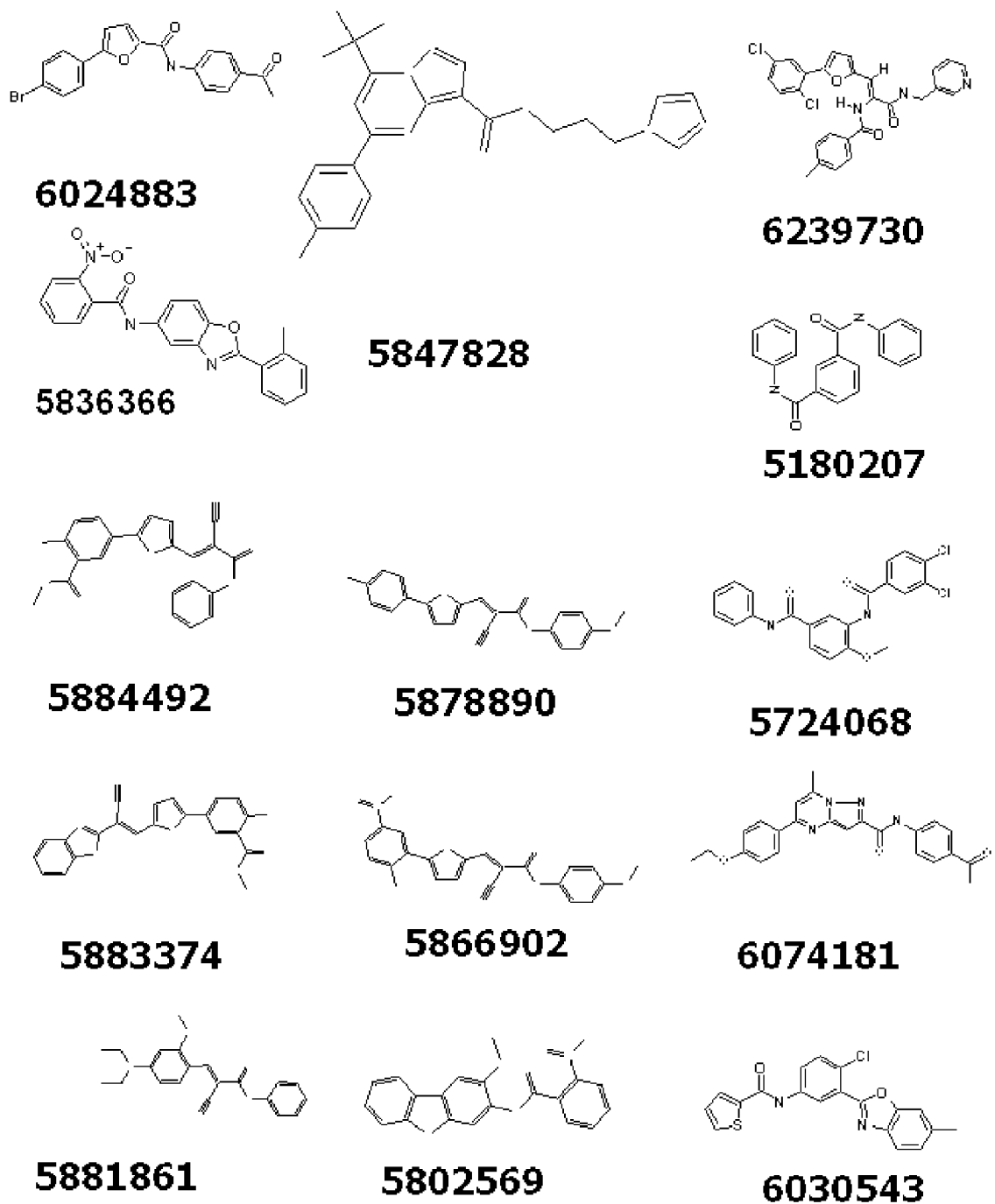
FIG. 7 shows several quorum sensing agonists of the present invention.
Figure 8A:
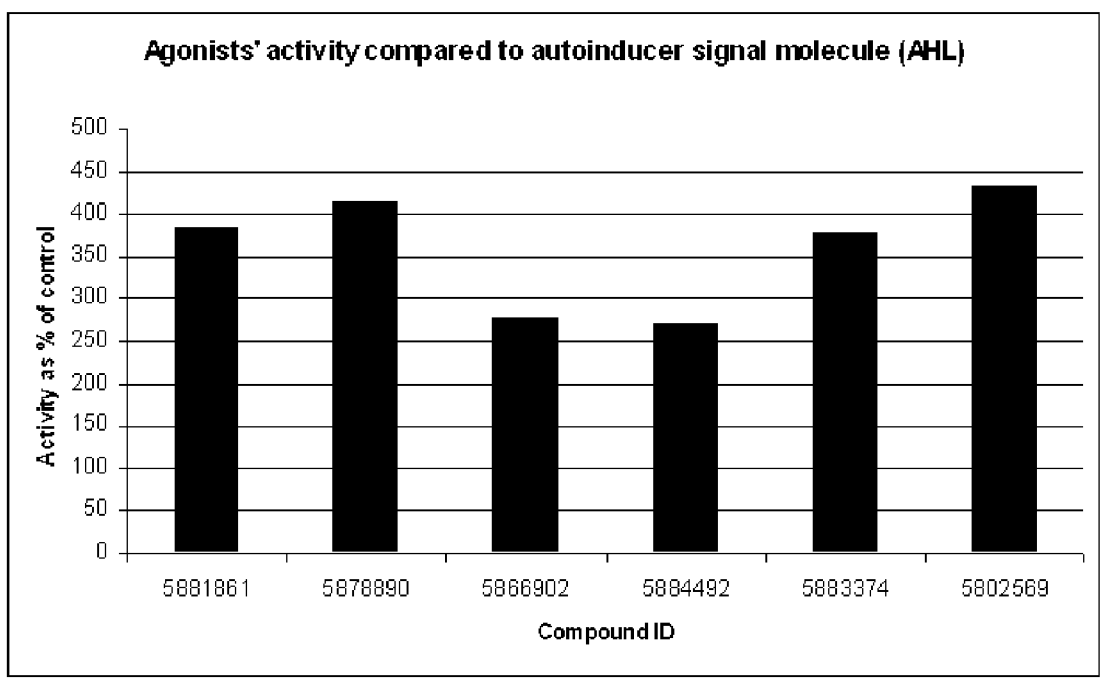
FIG. 8 shows that the agonists increase quorum sensing related gene expression as measured by GFP activity as a percentage of the AHL control.
Figure 8B:
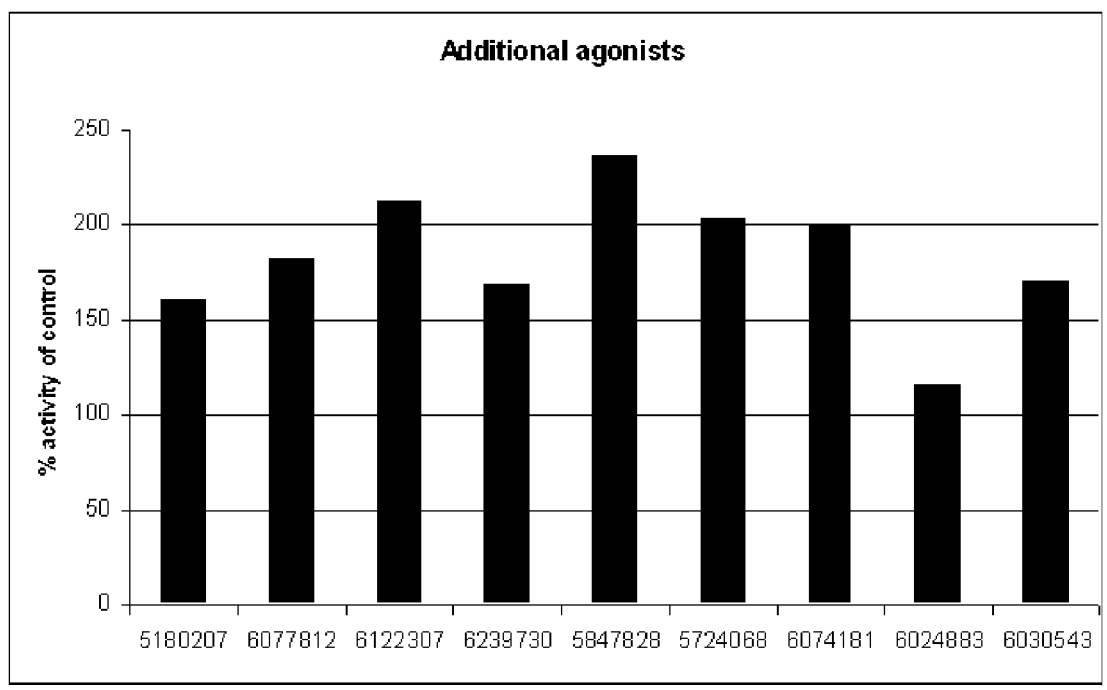
Figure 9:
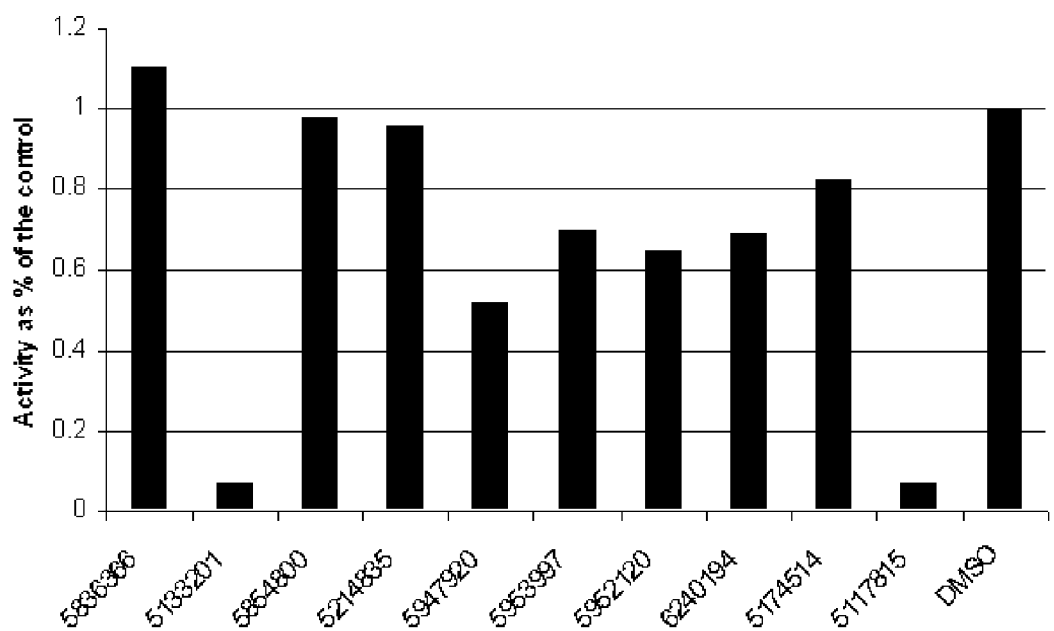
FIG. 9 shows that the antagonists of the present invention compete effectively with $3oxoC_{12}HSL$.
Figure 12:
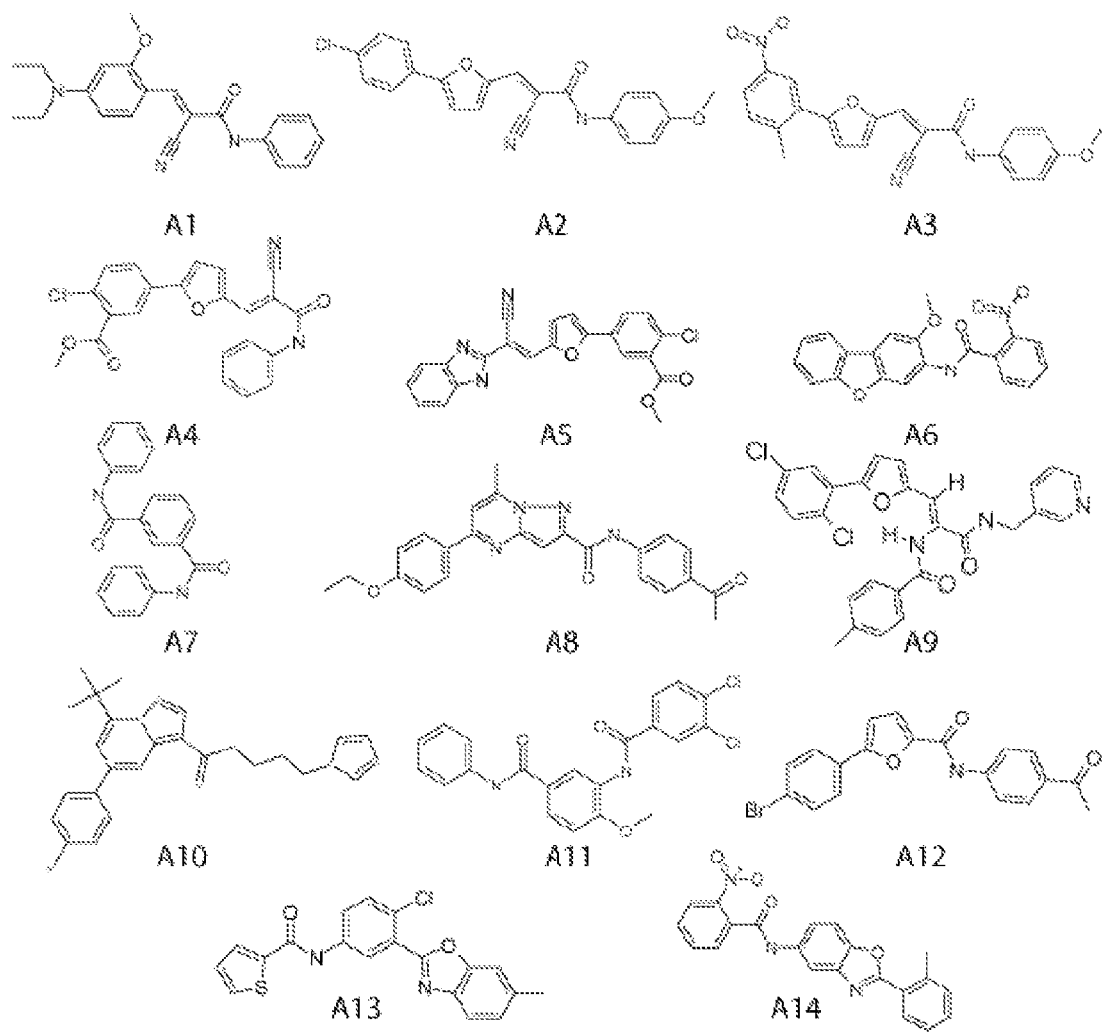
FIG. 12 depicts structures of Agonists compounds identified in the primary screen.
Figure 13:
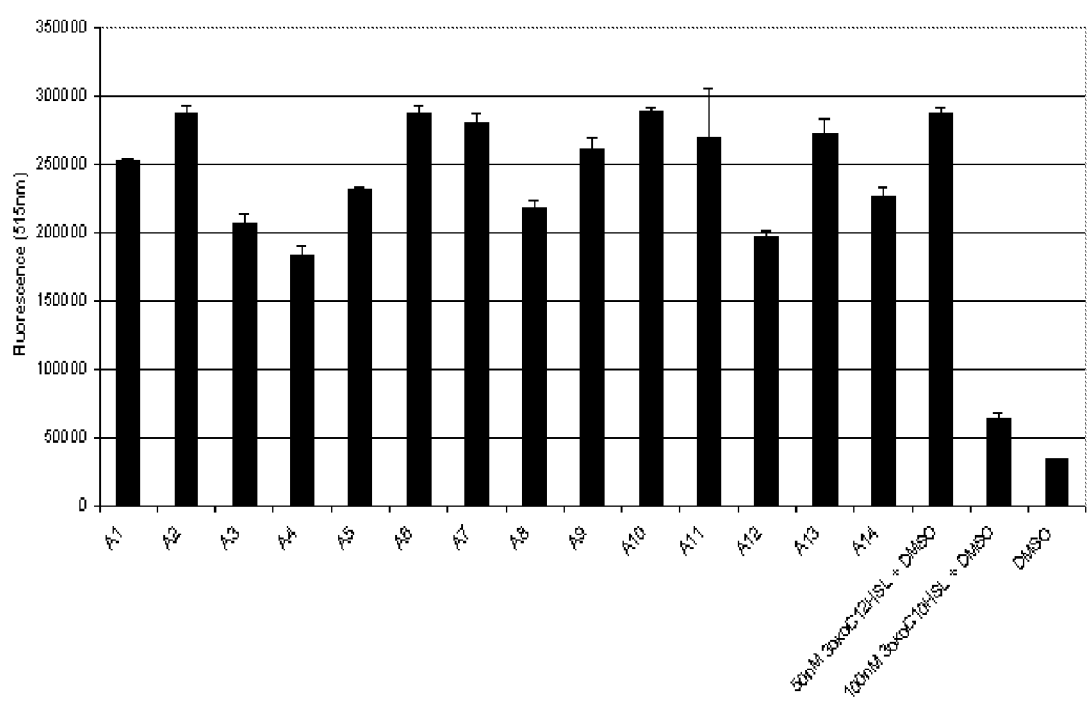
FIG. 13 depicts graph of Agonist activity as compared to synthetic AHLs.

Agonists that were identified in the preliminary screen were further characterized in the absence of exogenous AHL to determine their activity as agonists of LasR mediated gene expression. Reporter assays similar to those used in the secondary screens of antagonists were used to characterize the activity of the agonists. Representative results are presented in FIGS. 8A and B and present the percentage of GFP expression activity as a function of expression of the 100 nM AHL (3-oxo-C10 HSL) control. The numbers on the X axis refer to the Chembridge library reference number. Similarly, FIG. 13 presents agonist activity as compared to synthetic AHLs as a function of fluorescence units. Agonists appear to fall into two closely related families of compounds (A7, A11) (A2, A3, A4). Almost all of the agonists share some structural similarity. Table 2 presents a list of the Chembridge and antagonist/agonist numerical designations. FIGS. 7 and 12 present the structures of the antagonist compounds identified in this study. Comparison of the structures of the strongest antagonists and agonists suggest that the two classes of compounds are structurally distinct.

Table 3 presents the activities of agonists and antagonists in AHL reporter strains that utilize different LuxR-type activators. These results suggest that activity of the compounds is specific to the AHL reporter strains that are regulated by the LasR transcriptional activator but is not dependent on the host background.

TABLE 3

Activity of agonists and antagonists in AHL reporter strains that utilize different LuxR-type activators

| Strain | LuxR-type Activator | Agonists | Antagonists |
|---|---|---|---|
| *P. putida* F117 pKRC12 | LasR | + | + |
| *E. coli* MT 102 pJBA132 | LuxR | − | − |
| *E. coli* DH 10B pKRC12 | LasR | + | N.D. |
| *E. coli* DH 10B pJBA132 | Lux R | − | N.D. |
| *C. violaceum* CV026 | CviR | − | − |
| *A. tumefaciens* KYC55 | TraR | − | N.D. |

+ Activity as agonist or antagonist
— No activity
N.D. Not determined

EXAMPLE 2

Activity of Antagonists Compared in the Presence of Synthetic AHLs

This example presents representative results of experiments designed to test the activity of putative antagonists when challenged with different concentrations of synthetic AHLs, particularly 3oxoC12HSL. Assays were conducted with *P. putida* F117 pKRC12 reporter strain as described in the methods for secondary screens.

Figure 14:
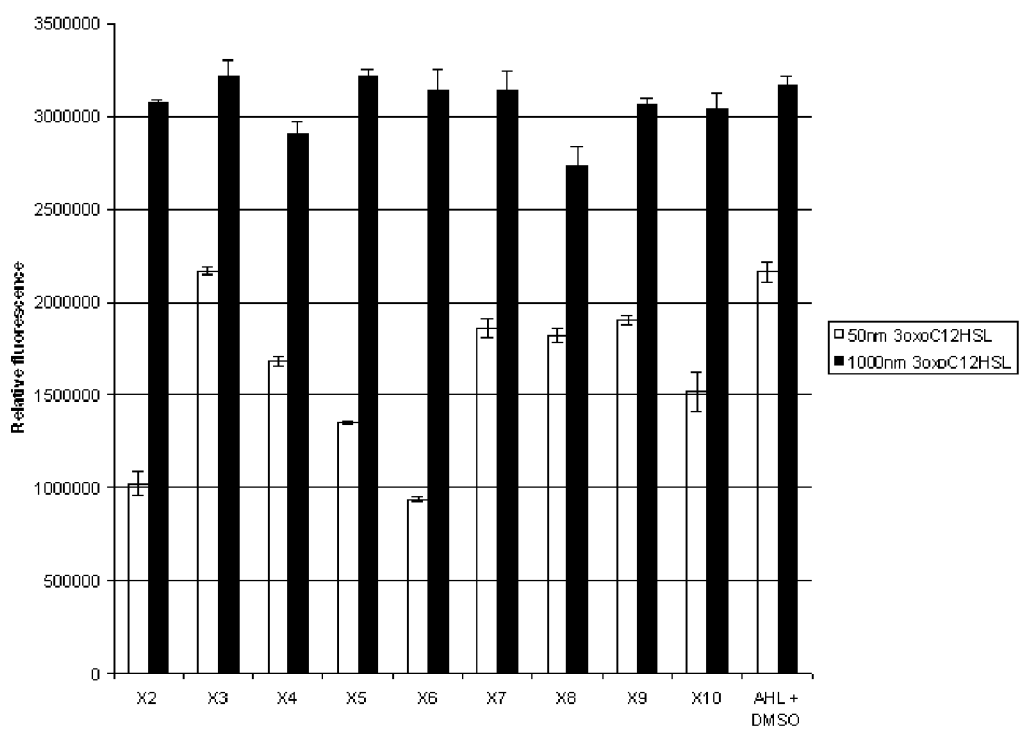
FIG. 14 depicts graph of Antagonists vs. increasing concentrations of $3oxoC_{12}HSL$.

Representative results of experiments designed to test the effects of increasing concentrations of synthetic AHLs are presented in FIG. 14 and suggest that increasing the concentration of 3oxoC12HSL to extremely high levels diminishes the activity of the antagonistic compounds. This reduction of the antagonistic activity with increasing concentrations of the synthetic AHLs suggests that these compounds are outcompeted by saturating concentrations of the cognate AHL and further suggests that these compounds may interact specifically with the LasR transcriptional activator.

Figure 15:
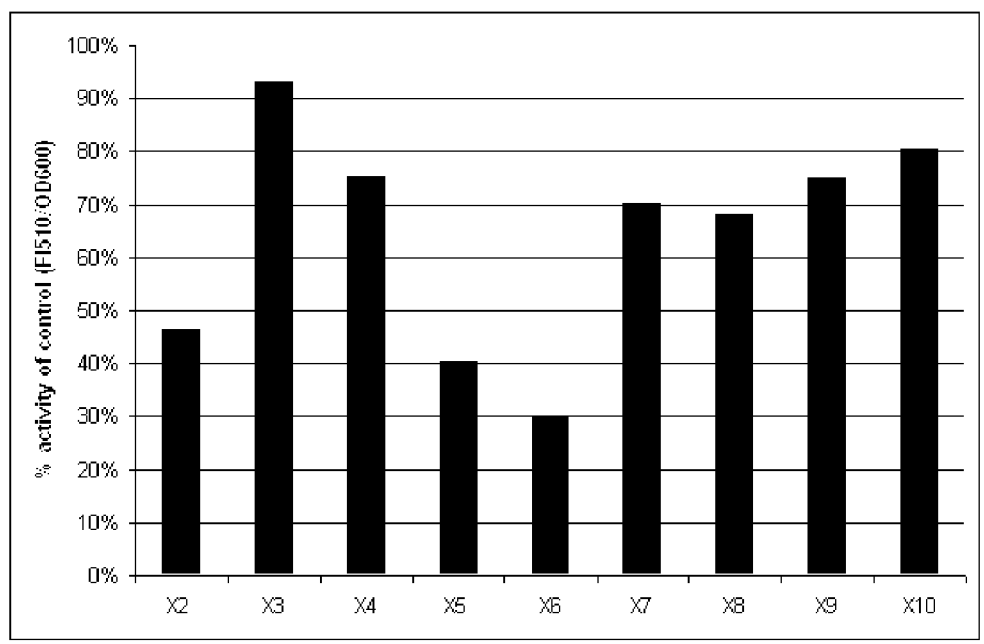
FIG. 15 depicts graph of 10 μM Antagonists vs. $3oxoC_{12}HSL$.

FIG. 15 presents the results of experiments designed to test antagonist activity at concentrations of 10 μM in the presence of 50 nM 3oxoC12HSL. These results suggest that compounds that these compounds are good candidates for antagonism of the interaction between LasR and 3oxoC12HSL.

EXAMPLE 3

Structure-Activity Analysis of Antagonists

Following the initial screens to identify strong antagonists of the LasR transcriptional activator, further investigation of additional compounds in the Chembridge library was carried out. In particular, the experiments described in Example 1 identified three compounds that shared a thiocarbamate structure, as also shown in FIG. 16. To further investigate structure-activity relationships, the inventors examined the antagonist activity of 19 additional compounds with related thiocarbamate structures, using the procedures described in Example 1. The results are presented in Table 4, expressed as the percent activity of the AHL induced control. The % activity represents the relative fluorescence, which is the fluorescence observed in each assay divided by bacterial cell density as measured by absorbance at 600 nm. Compounds were assayed at a concentration of 10 μM. Assays were conducted with *P. putida* F117 pKRC12 reporter strain as described in the methods for secondary screens. The 3oxoC10HSL and 3oxoC12HSL were assayed at concentrations of 100 nM and 50 nM, respectively.

The results suggest that compounds appear to have altered specificity in their antagonism when challenged with different AHLs. Furthermore, ester substitutions at the ortho position of the aniline ring provide the greatest activity against 3oxoC12HSL.

TABLE 4

Structure activity relationships(SAR) of thiocarbamate antagonists in competition with 3oxoC12HSL or 3oxoC10HSL:

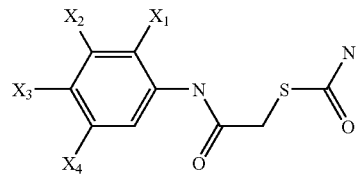

| | | | | | % Activity of AHL Standard | |
|---|---|---|---|---|---|---|
| Compound | $X_1$ | $X_2$ | $X_3$ | $X_4$ | 3 oxo C12HSL | 3 oxo C10HSL |
| 1 | COOCH$_3$ | | | | 33.64 | 35.86 |
| 2 | COOCH$_2$CH$_3$ | | | | 40.09 | 35.50 |
| 3 | | | CH$_3$ | Cl | 41.63 | 32.27 |
| 4 | CH$_3$ | CH$_3$ | | | 43.00 | 37.50 |
| 5 | CH$_3$ | | | Cl | 47.85 | 56.73 |
| 6 | | OH | | | 49.68 | 45.08 |
| 7 | | | OCH$_3$ | | 49.85 | 36.45 |
| 8 | Cl | | | | 51.98 | 32.72 |
| 9 | | OCH$_3$ | | | 53.30 | 35.50 |
| 10 | | CH$_3$ | | | 55.40 | 49.10 |
| 11 | Br | | | | 56.70 | 36.60 |
| 12 | | | COCH$_3$ | | 64.90 | 59.20 |

TABLE 4-continued

Structure activity relationships (SAR) of thiocarbamate antagonists in competition with 3oxoC12HSL or 3oxoC10HSL:

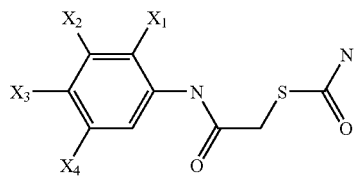

| | | | | | % Activity of AHL Standard | |
|---|---|---|---|---|---|---|
| Compound | $X_1$ | $X_2$ | $X_3$ | $X_4$ | 3 oxo C12HSL | 3 oxo C10HSL |
| 13 | | F | | | 67.60 | 33.60 |
| 14 | $OCH_3$ | | | | 68.60 | 46.80 |
| 15 | | | Br | | 70.10 | 39.00 |
| 16 | $OCH_3$ | | $OCH_3$ | | 70.90 | 35.00 |
| 17 | | | | I | 81.20 | 67.20 |
| 18 | $CH_3$ | | $CH_3$ | | 82.30 | 40.00 |
| 19 | OH | | | | 82.90 | 38.60 |
| 20 | | Cl | Cl | | 87.70 | 40.50 |
| 21 | | Cl | | | 88.50 | 43.30 |
| 22 | | | $COOCH_3$ | | 101.0 | 57.60 |

The results suggest that compounds appear to have altered specificity in their antagonism when challenged with different AHLs. Furthermore, ester substitutions at the ortho position of the aniline ring provide the greatest activity against 3oxoC12HSL.

EXAMPLE 4

*Caenorhabditis elegans* Nematode Model for Testing Compounds

*P. aeruginosa* strains, PA01 wild type virulent and a virulent PA01 laslrhll mutant strain were grown in 5 ml of LB liquid culture in 18 mm testtubes in the presence or absence of 10 μm experimental compound overnight with shaking. 15 μl samples of bacterial culture are spread on 55 mm BHI agar plates containing 10 μm experimental compound or no compound as a control.

Following overnight incubation at 28° C., ten L4 or adult wild-type Bristol N2 nematodes were transferred to the plates, which were then sealed with parafilm and incubated at 20° C. The number of living worms per plate was determined at various time points with a compound microscope. Nematodes are considered dead when they fail to move in response to the tapping of the plate against the microscope stage.

Expected Results:

Nematodes treated with the wild type pathogen PA01 in the absence of antagonistic compounds will suffer 100% mortality. Nematodes treated with the wild type pathogen PA01 and antagonistic compounds should suffer less than 50% mortality. Nematodes that are treated with the avirulent PA01 laslrhll will suffer 0% mortality in the presence or absence of compounds.

The foregoing description and examples have been set forth merely to illustrate the invention and are not intended to be limiting. Since modifications of the disclosed embodiments incorporating the spirit and substance of the invention may occur to persons skilled in the art, the invention should be construed broadly to include all variations falling within the scope of the appended claims and equivalents thereof. All references cited hereinabove and/or listed below are hereby expressly incorporated by reference.

REFERENCES (1) Hentzer, M., and M. Givskov. 2003. Pharmacological inhibition of quorum sensing for the treatment of chronic bacterial infections. J Clin Invest 112:1300-7.

(2) Pearson, J. P., E. C. Pesci, and B. H. Iglewski. 1997. Roles of *Pseudomonas aeruginosa* las and rhl quorum-sensing systems in control of elastase and rhamnolipid biosynthesis genes. J Bacteriol 179:5756-67.

(3) Van Delden, C., and B. H. Iglewski. 1998. Cell-to-cell signaling and *Pseudomonas aeruginosa* infections. Emerg Infect Dis 4:551-60.

(4) Steidle, A., K. Sigl, R. Schuhegger, A. Ihring, M. Schmid, S. Gantner, M. Stoffels, K. Riedel, M. Givskov, A. Hartmann, C. Langebartels, and L. Eberl. 2001. Visualization of N-acylhomoserine lactone-mediated cell-cell communication between bacteria colonizing the tomato rhizosphere. Appl Environ Microbiol 67:5761-70.

(5) Andersen, J. B., A. Heydorn, M. Hentzer, L. Eberl, O. Geisenberger, B. B. Christensen, S. Molin, and M. Givskov. 2001. gfp-based N-acyl homoserine-lactone sensor systems for detection of bacterial communication. Appl Environ Microbiol 67:575-85.

(6) Rasmussen, T. B., T. Bjarnsholt, M. E. Skindersoe, M. Hentzer, P. Kristoffersen, M. Kote, J. Nielsen, L. Eberl, and M. Givskov. 2005. Screening for quorum-sensing inhibitors (QSI) by use of a novel genetic system, the QSI selector. J Bacteriol 187:1799-814.

(7) Rand, J. B., and C. D. Johnson. 1995. Genetic pharmacology: interactions between drugs and gene products in *Caenorhabditis elegans*. Methods Cell Biol 48:187-204.

What is claimed is:

1. A method for inhibiting quorum sensing of a Gram negative bacterium that comprises a LasR transcriptional activator, comprising contacting said Gram negative bacte rium with at least one quorum sensing compound having the structural formula:

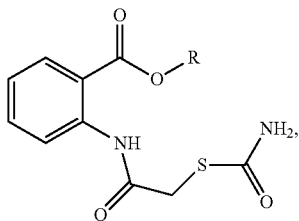

wherein R is —$(CH_2)_nH$ and n is 1, 2, 3, 4, or 5, or a pharmaceutically acceptable salt thereof; whereby quorum sensing by said Gram negative bacterium is inhibited by said compound.

2. The method according to claim 1, wherein the quorum sensing compound is:

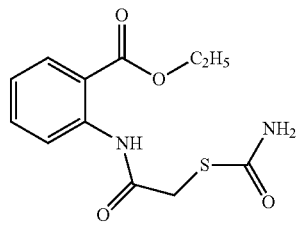

or a pharmaceutically acceptable salt thereof.

3. The method according to claim 1, wherein the quorum sensing compound is:

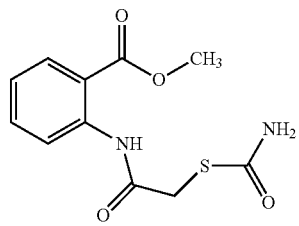

or a pharmaceutically acceptable salt thereof.

4. The method according to claim 1, wherein the bacterium is *Pseudomonas aeruginosa*.

5. A method according to claim 1, further comprising contacting said Gram negative bacterium with an antibiotic selected from the group consisting of aminoglycosides, β-lactam antibiotics, and fluoroquinolones.

6. A pharmaceutical composition comprising (a) a compound having the structural formula:

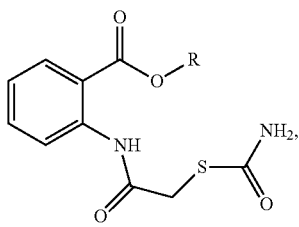

wherein R is —$(CH_2)_nH$ and n is 1, 2, 3, 4, or 5; or
(b) a pharmaceutically acceptable salt of said compound; and
(c) a pharmaceutically-acceptable carrier.

7. The pharmaceutical composition of claim 6, wherein the compound is:

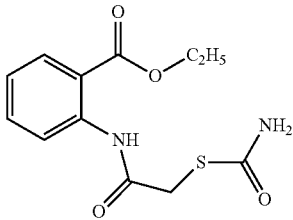

or a pharmaceutically acceptable salt thereof.

8. The pharmaceutical composition of claim 6, wherein the compound is:

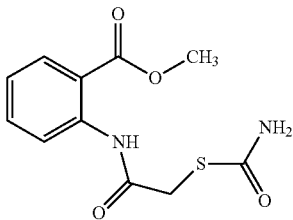

or a pharmaceutically acceptable salt thereof.

9. The pharmaceutical composition according to claim 6, further comprising an antibiotic selected from the group consisting of aminoglycosides, β-lactam antibiotics, and fluoroquinolones.

10. A method for reducing biofilm formation on a surface, the method comprising administering to said surface a quorum sensing compound having the structural formula:

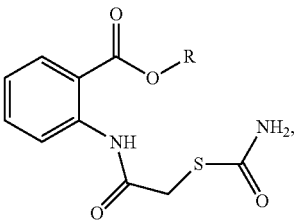

wherein R is —$(CH_2)_nH$ and n is 1, 2, 3, 4, or 5, or a salt thereof; whereby biofilm formation is reduced on said surface by said compound.

11. The method of claim 10, wherein the quorum sensing compound is:

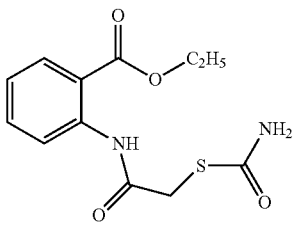

or a salt thereof.

12. The method according to claim 10, wherein the quorum sensing compound is:

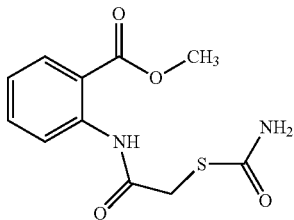

or a salt thereof.

13. A method according to claim 10, further comprising administering to said surface an antibiotic selected from the group consisting of aminoglycosides, β-lactam antibiotics, and fluoroquinolones.

14. A method for reducing the virulence of a Gram negative bacterium that comprises a LasR transcriptional activator, the method comprising contacting said Gram negative bacterium with a quorum sensing compound having the structural formula:

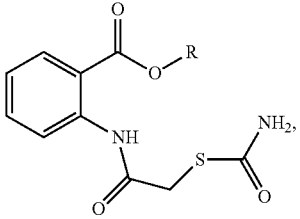

wherein R is —$(CH_2)_n$H and n is 1, 2, 3, 4, or 5, or a salt thereof; whereby the virulence of said Gram negative bacterium is reduced by said compound.

15. The method of claim 14, wherein the quorum sensing compound is:

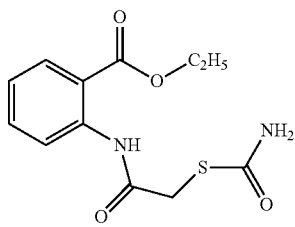

or a salt thereof.

16. The method according to claim 14, wherein the quorum sensing compound is:

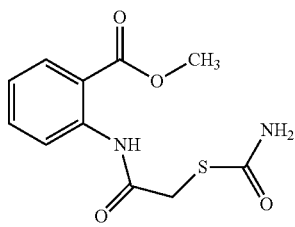

or a salt thereof.

17. A method according to claim 14, further comprising contacting said Gram negative bacterium with an antibiotic selected from the group consisting of aminoglycosides, β-lactam antibiotics, and fluoroquinolones.

18. A method of increasing disease resistance to a Gram negative bacterial disease or reducing susceptibility to a Gram negative bacterial disease in a subject, wherein the Gram negative bacteria causing the disease comprise a LasR transcriptional activator, comprising the step of contacting a subject with a quorum sensing compound having the structural formula:

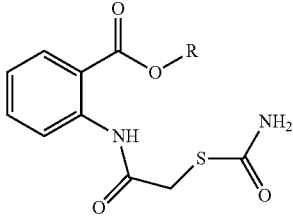

wherein R is —$(CH_2)_n$H and n is 1, 2, 3, 4, or 5, or a salt thereof; whereby the Gram negative bacterial disease resistance is increased or susceptibility to the Gram negative bacterial disease is reduced in said subject by said compound.

19. The method of claim 18, wherein the quorum sensing compound is:

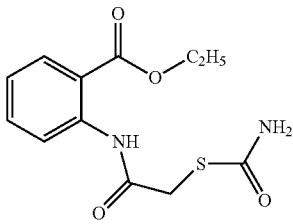

or a salt thereof.

20. The method according to claim 18, wherein the quorum sensing compound is:

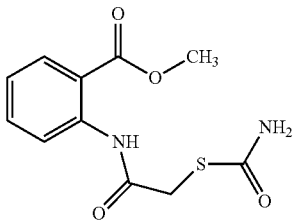

or a salt thereof.

21. A method according to claim 18, further comprising contacting said subject with an antibiotic selected from the group consisting of aminoglycosides, β-lactam antibiotics, and fluoroquinolones.

22. A method for inhibiting quorum sensing of a Gram negative bacterium that comprises a LasR transcriptional activator, comprising contacting said bacterium with at least one quorum sensing compound having the structural formula:

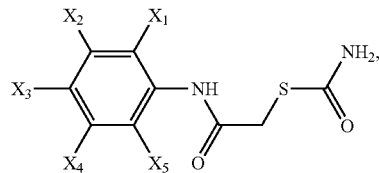

wherein $X_1$, $X_2$, $X_3$, $X_4$, and $X_5$ are independently selected from the group consisting of H, OH, F, Cl, Br, I, $OR_1$, $COOR_1$, and $R_1$, wherein $R_1$ is $(CH_2)_n$H and n is an integer between 0 and 5.

* * * * *